(12) United States Patent
Allsworth et al.

(10) Patent No.: US 10,952,640 B2
(45) Date of Patent: Mar. 23, 2021

(54) METHOD FOR COLLECTING A SELECTIVE PORTION OF A SUBJECT'S BREATH

(71) Applicant: Owlstone Medical Limited, Cambridge (GB)

(72) Inventors: Max Allsworth, Essex (GB); Duncan Apthorp, Cambridge (GB); Marc Van Der Schee, Amsterdam (NL); Rob Smith, Cambridgeshire (GB); Jasper Boschmans, Cambridge (GB); Simon Kitchen, Cambridge (GB)

(73) Assignee: Owlstone Medical Limited, Cambridge (GB)

( * ) Notice: Subject to any disclaimer, the term of this patent is extended or adjusted under 35 U.S.C. 154(b) by 486 days.

(21) Appl. No.: 15/494,973

(22) Filed: Apr. 24, 2017

(65) Prior Publication Data
US 2017/0303823 A1    Oct. 26, 2017

Related U.S. Application Data

(60) Provisional application No. 62/327,185, filed on Apr. 25, 2016.

(51) Int. Cl.
*A61B 5/097* (2006.01)
*A61M 16/08* (2006.01)
(Continued)

(52) U.S. Cl.
CPC .............. *A61B 5/097* (2013.01); *A61B 5/082* (2013.01); *A61B 5/0833* (2013.01); *A61B 5/0836* (2013.01); *A61B 5/091* (2013.01); *A61B 5/486* (2013.01); *A61B 5/6803* (2013.01); *A61B 5/7203* (2013.01); *A61B 5/7285* (2013.01); *A61B 10/00* (2013.01); *A61M 16/06* (2013.01); *A61M 16/085* (2014.02); *A61B 5/0803* (2013.01); *A61B 5/085* (2013.01);
(Continued)

(58) Field of Classification Search
CPC ..... A61B 5/083; A61B 5/0833; A61B 5/0836; A61B 5/097; A61B 5/7203; A61B 5/7207; A61M 16/06; A61M 16/0605; A61M 16/0611; A61M 16/0616; A61M 16/0622; A61M 2016/0027
See application file for complete search history.

(56) References Cited

U.S. PATENT DOCUMENTS

| | | | | |
|---|---|---|---|---|
| 6,017,315 | A * | 1/2000 | Starr ................ | A61M 16/06 600/529 |
| 2010/0143880 | A1* | 6/2010 | Stockmann ....... | A61M 16/0858 435/4 |

(Continued)

OTHER PUBLICATIONS

Annex to Communication Relating to the Results of the Partial International Search in PCT/GB2017/051119.

*Primary Examiner* — Carrie R Dorna
(74) *Attorney, Agent, or Firm* — Barnes & Thornburg LLP

(57) ABSTRACT

Disclosed is a method for selectively capturing one or more portions of a patient's breath, comprising:
 detect one or more parameters regarding the patient's breath during a breathing routine;
 determine one or more data points from the detected one or more parameters wherein the one or more data points identifies one or more portions of the patient's breath to capture; and
 capture one or more portions of the patient's breath during the breathing routine.

34 Claims, 15 Drawing Sheets

(51) Int. Cl.

| | |
|---|---|
| *A61B 5/08* | (2006.01) |
| *A61M 16/06* | (2006.01) |
| *A61B 5/083* | (2006.01) |
| *A61B 5/091* | (2006.01) |
| *A61B 5/00* | (2006.01) |
| *A61B 10/00* | (2006.01) |
| *A61B 5/085* | (2006.01) |
| *A61M 16/00* | (2006.01) |

(52) U.S. Cl.
 CPC ............... *A61B 2010/0087* (2013.01); *A61B 2560/0475* (2013.01); *A61M 2016/0027* (2013.01); *A61M 2202/0208* (2013.01); *A61M 2205/7518* (2013.01); *A61M 2230/005* (2013.01); *A61M 2230/432* (2013.01); *A61M 2230/435* (2013.01)

(56) References Cited

U.S. PATENT DOCUMENTS

| | | |
|---|---|---|
| 2014/0194703 A1 | 7/2014 | Wondka |
| 2014/0228699 A1 | 8/2014 | Causevic et al. |
| 2015/0265184 A1 | 9/2015 | Wondka |
| 2015/0335267 A1 | 11/2015 | Cormier |

\* cited by examiner a) GC-MS results from two breath samples including retention time matched and NIST identification. b) GC-FAIMS Quality Control

Main Screen | Collection settings

End upper airway threshold
◇ [ 1 ]

Start upper airway threshold
◇ [ 5 ]

Start lower airway threshold
◇ [ 7 ]

Set positive to collect more breath, negative to collect less (range -100 to 100)

Initial wait before learn
◇ [ 4 ] Seconds

Maximum learn time
◇ [ 30 ] Seconds

Error checking
☐ CO2 High check
☐ CO2 Low check
☐ Leak alarm
☐ Collect during erratic breathing
☐ Check all EEPROM values
☐ Only run if calibration dates valid CO2 low alarm
◇ [ 1 ] %

CO2 high alarm
◇ [ 7 ] %

METHOD FOR COLLECTING A SELECTIVE PORTION OF A SUBJECT'S BREATH

FIELD OF THE INVENTION

The present invention relates generally to a method for collecting a sample of a selective portion of a subject's breath, which sample may be used, for example, to facilitate diagnosis of medical conditions based on biomarker analysis, and in particular, to a method that collects volatile biomarkers from breath for assessment of health and disease diagnosis, monitoring and assessment of prognosis.

BACKGROUND OF THE INVENTION

The metabolome is the aggregate of small molecules that originate from metabolic processes throughout the body. Metabolomic analysis is appealing for biomedical applications as relatively small changes in gene-expression or protein activity can have a profound effect on the concentrations of downstream metabolites. A significant fraction of these metabolites are volatile. These biomarkers are of specific interest in health and disease as they are excreted through breath, urine, feces and skin providing non-invasive access. Volatile biomarkers (VBs) consist of both volatile organic compounds (VOCs) and volatile inorganic compounds (VICs). Examples of VBs implicated in health and disease include alkanes, alkenes, acetone, isoprene, NO, CO and aldehydes.

Any change in the function of an organism changes cellular metabolism by definition. Consequently this affects the metabolome and its volatile fraction. The resulting changes in VBs may therefore serve as biomarkers for assessment of a wide range of normal physiological, and pathophysiological, processes.

The rate at which VBs are exhaled is the net effect of several interacting (bio)chemical processes: intra and extracellular degradation, solubility of the compound in extracellular fluid, fat and blood, the affinity with extracellular matrix and carrier proteins, the concentration gradient between the alveolar and bronchial air, the vapor pressure and alveolar ventilation. This results in a chemical equilibrium of a given compound between breath, blood and fat which can be described by that substance's physiochemical partition constant.

To date several thousands of individual VBs have been identified generally occurring in the parts per million/parts per billion range. VBs may be of local, systemic or exogenous origins (FIG. 1).

In breath, locally produced compounds diffuse directly into alveoli or the airway lumen along the respiratory tract. An example is the biological mechanism behind VOC formation in the presence of Reactive Oxygen Species (ROS). ROS are responsible for increased levels of oxidative stress associated with disease in general. ROS drive cell wall lipid peroxidation resulting in production of ethane and n-pentane. These substances show only low solubility in blood and are therefore excreted into breath within minutes of their formation in tissues. Hence, exhaled concentrations of ethane and n-pentane can be used to monitor the degree of oxidative damage in the body.

Volatiles of systemic origins are derived from the circulation after originating from metabolic processes elsewhere and dissolving into the blood. Therefore, even non-pulmonary diseases contribute to exhaled VBs, which has successfully been used in the assessment of non-pulmonary malignancies. A well known group of systemically originating VOCs are ketone bodies like acetone, acetoacetate and hydroxybutyrate which are oxidized via the Krebs cycle in peripheral tissue as part of glucose metabolism.

Exogenous VBs can be inhaled or absorbed through the skin. They primarily originate from non-human sources and exist in three categories. Firstly, VBs that are in- and expired without any interaction with the body. A second group of exogenous VBs does interact with human tissue and can be stored inside the body for extensive periods of time. The latter volatiles can therefore serve as potential biomarkers for environmental exposures and buildup of toxins such as the cigarette smoke carcinogen N-Nitrosamine. The third group of exogenous VBs is of (resident) microbial origin (predominantly bacteria, but also fungi and viruses), making them of specific interest when identifying infectious diseases or diseases linked to changes in microbiome. Since exhaled VBs reflect this broad range of (patho) physiological processes they have potential usage in one or more of the following: 1) assessment of normal metabolic processes; 2) evaluation of environmental exposure; 3) therapy stratification; 4) monitoring of therapy response; 5) monitoring of disease activity and exacerbation prediction; 6) identification and characterization of micro-organisms in a host; 7) assessment of host response to micro-organisms; 8) screening for pre-morbid conditions; and 8) early detection of disease in asymptomatic subjects. It is to be appreciated these potential applications are relevant in pulmonary and non-pulmonary diseases.

However, it is also to be appreciated that although analysis of body fluids (e.g., blood, sputum, urine) for disease diagnoses and monitoring is routine clinical practice, human breath analysis methodologies that exploit the non-invasive nature of such diagnoses are still under-developed and have not been adopted in clinical practice. Some of the underlying reasoning regarding this lack of adoption includes: 1) reproducibility of technology (most techniques used to date show inadequate inter and intra device reproducibility to allow deployment); 2) technology sensitivity (VBs, especially VOCs typically occur in the ppb ppt range, many analytical systems do not have this sensitivity); 3) selectivity of technology (as the composition of VBs is complex, a system needs to be selective in detection of target compounds), 4) unreliable sample collection (sample collection is generally poorly standardised and validated); and 5) technology costs (costs of classical chemical analytical instruments are prohibitive for deployment of a VB based test).

SUMMARY OF THE INVENTION

The purpose and advantages of the below described illustrated embodiments will be set forth in and apparent from the description that follows. Additional advantages of the illustrated embodiments will be realized and attained by the devices, systems and methods particularly pointed out in the written description and claims hereof, as well as from the appended drawings.

To achieve these and other advantages and in accordance with the purpose of the illustrated embodiments, in a first aspect, the invention provides a method for selectively capturing one or more portions of a patient's breath, comprising: detect one or more parameters regarding the patient's breath during a breathing routine; determine one or more data points from the detected one or more parameters wherein the one or more data points identifies one or more portions of the patient's breath to capture; and capture one or more portions of the patient's breath during the breathing routine.

The invention also provides a method for selectively capturing one or more portions of a subject's breath, the method comprising the steps of: measuring, in absolute or relative terms, at least once, during each sampled breath cycle of a subject at least one parameter relating to the subject's breathing; and using the aforementioned measurement or measurements to identify and selectively sample one or more desired portions of the subject's breath. For convenience, this is referred to herein as the second aspect of the invention. Preferably the at least one parameter will be measured a plurality of times during each sample of breath cycle of the subject. Conveniently the method will be in accordance with the method of the first aspect of the invention defined in the preceding paragraph.

In the first aspect, the step of "detect one or more parameters regarding the patient's breath during a breathing routine" substantially corresponds to the step of "measuring in absolute or relative terms, at least once during each sampled breath cycle of a subject, at least one parameter relating to the subject's breathing" in the second aspect of the invention. Similarly, in the first aspect, the step of "determine one or more data points from the detected one or more parameters wherein the one or more data points identifies one or more portions of the patient's breath to capture" substantially corresponds to the step of "using the aforementioned measurement or measurements to identify and selectively sample one or more desired portions of the subject's breath" in the second aspect of the invention.

The methods defined above are conveniently performed using a portable microprocessor-controlled breath collection apparatus which collects pre-specified fractions of in- or expired air (e.g. alveolar) VBs into sorbent tubes which are then analyzed by chemical analytical techniques such as Gas Chromatography and Mass Spectrometry and Ion-Mobility Spectrometry (IMS) techniques, and in particular, Field Asymmetric Ion Mobility Spectrometry (FAIMS) techniques, for disease diagnosis.

In crude terms, the method of the invention makes use of the fact that air exhaled from a subject at different phases of the exhalation is relatively enriched in gases that emanate from different parts of the patient's body. For example, breath that is exhaled in the initial phase of the exhalation tends to be relatively enriched in gas from the subject's mouth and/or pharyngeal region; breath exhaled a little later in the exhalation tends to be enriched in gases from the subject's trachea and bronchioles; and breath exhaled even later in the exhalation tends to be relatively enriched in gas from the subject's alveoli.

However, as different subjects breathe at different rates, and have respiratory systems with different volumes etc., it is not possible to rely, for example, on a simple time-based method to determine which portion of a subject's breath to selectively capture or sample for analysis if particular fractions of the subject's exhaled breath are of interest.

Instead, the method of the invention measures at least one, preferably at least two, parameters relating to the subject's breathing cycle, in order to determine when to sample exhaled air during the subject's breathing cycle, in order to determine when to sample the subject's exhaled breath so as selectively to obtain exhaled air samples which are relatively enriched with gases emanating from particular parts of the subject's body. The method of the invention will typically also measure time.

The method is typically performed using a human subject, but could conceivably be used to selectively sample breath from an animal, such as a horse (e.g. a high value race horse) or a farm livestock (e.g. high value animals such as bulls kept for breeding purposes).

The invention is described below in relation to measurement of at least one parameter etc. as referred to in the method of the second aspect of the invention. It will be appreciated however that this description is also applicable to the "detection of one or more parameters" as set out in the method of the first aspect of the invention.

More usually the method will be used with an adult human subject (male or female), but is also sufficiently flexible to be used with adolescent or juvenile human subjects.

The method of the invention measures at least one parameter relating to the subject's breathing in order to identify, preferably essentially in "real time", at what stage in the breath cycle the subject may be at any point in time, at least during exhalation, and optionally also during inhalation. It may be preferred to measure more than one parameter, in order to improve the accuracy of the identification of the stage of the breath cycle. More especially the one or more selected parameters will conveniently be measured a plurality of times during each breath cycle. Advantageously the one or more parameters will be measured many times per second, so as to perform substantially continuous monitoring of the one or more selected parameters, at least during exhalation and optionally also during inhalation.

The one or more parameters may comprise: an absolute pressure measurement; a relative pressure measurement; an $O_2$ partial pressure measurement; a $CO_2$ partial pressure measurement.

More specifically, the method may involve calculation of values derived from the measured parameter. Further, it is generally preferred to utilise, or calculate a relative measurement. This is because, for example, absolute measurements will vary between different individuals depending on numerous factors such as, age, sex, pulmonary health and efficiency, history of smoking or previous lung disease etc.

In a preferred embodiment, the method involves measuring the amplitude or pressure difference between peak and trough in absolute pressure in a breath cycle, and optionally calculating or determining therefrom the $1^{st}$ differential of the pressure (i.e. the rate of change of pressure at any given moment). These parameters are preferably measured many times a second (e.g. about every 100 milliseconds (m/s)), so as to be substantially continuously monitored.

The measured parameter(s), and/or values derived therefrom, may be compared with stored threshold values. When the measured parameter(s) and/or the values derived therefrom exceed or fall below the respective stored thresholds, as appropriate, this triggers the apparatus to start and stop collecting exhaled air, thereby selectively sampling a desired portion of the subject's breath.

The threshold values may be stored in a digital electrical memory component of the breath-sampling apparatus. In one embodiment, the value of one or more of the stored thresholds may be adjusted during sampling, in order to take account of the subject's breathing pattern or changes therein.

The selective sampling may involve, for example, opening or closing one or more valves, and/or operating or halting a pump or the like, so as to allow the exhaled breath representative of the desired portion to be captured on a capture device (such as a sorbent tube) or otherwise stored for subsequent analysis.

As noted above, the method of the invention is preferably performed using adult human subjects, but it can be used with younger subjects, e.g. juveniles (11-16 years old) or children (6-10 years old). Such younger subjects represent a challenge, especially children, as they generally breathe more shallowly and more rapidly than adults and the algorithms used to control operation of the breath sampling apparatus, which are designed for use with adult subjects, need modification for use with younger subjects. Preferably therefore the method of the invention may include the step of inputting information into a digital electronic memory or control device which controls operation of the breath sampling apparatus, the information being data regarding the subject. This may include, for example, one or more of the following: subject age; subject weight; and information about the subject's medical history and/or current suspected or known medical conditions.

In a particular embodiment, the inventors have devised one modified algorithm for use with children (6-10 years old) and a second modified algorithm for use with juveniles (11-16 years old), in which trigger points (i.e. to start and stop sample collection during a breath cycle) and scaling are adjusted appropriately.

In addition warnings generated by the breath sampling apparatus about breathing rate and fit of the apparatus mask to the subject can be modified by inputting the subject's weight—this correlates well with the expected pressure inside the mask, which allows the apparatus to distinguish between a small subject and a large subject with a poorly-fitting face mask.

It is not possible to obtain portions of exhaled breath which consist exclusively of, for example, alveolar air or bronchiolar air, since there is inevitably mixing of these fractions in the subject's respiratory tract during breathing. However, the method of the invention is able to selectively sample portions of the subject's exhaled breath which are enriched with e.g. bronchiolar air or alveolar air. Thus, in particular, the method of the invention is able to identify and selectively sample "upper" and "lower" breath portions which are relatively enriched for bronchiolar- and alveolar-originating air respectively.

The method of the invention typically requires sampling to be performed intermittently over a period of several minutes, in order to collect enough sample to obtain detectable amounts of biomarkers or other analytes of interest, since these are present in exhaled breath only at low concentration (e.g. typically 10-20 parts per million at most, often parts per billion). The method thus typically involves selectively sampling for a short period of time (e.g. about 2 seconds) in each of a plurality of breathing cycles. As an illustration, the duration of sampling is typically about 10 minutes (e.g. 8-10 minutes or longer, up to about 8-12 minutes), in which time the average adult human subject will exhale about 140 times (14 breaths per minute). A desired fraction of exhaled breath will be collected for about 1.5-2.0 seconds during each of these exhalations (except for exhalations which are disrupted by events such as sneezing or coughing).

Disclosed herein is an apparatus, system and method which collects and analyses biomarkers for the assessment of physiological and pathophysiological processes in health and disease (e.g. infectious, inflammatory and neoplastic disease) in an organism, including a human subject (hereinafter collectively referred to as a "patient"). In one or more illustrated embodiments, a measured quantity of breath (or other source of VBs) from a patient is collected, which is subsequently analyzed to detect the presence of VBs for assessment of metabolism in health and disease.

Therefore, it is to be appreciated that an object of the present invention is to collect one or more samples of the VB's (including VOCs and VICs) in a patient's breath for subsequent in vitro analysis. A purpose for collecting the VOC samples is to facilitate the diagnosis, monitoring and prognosis prediction of inflammatory, infectious and neoplastic diseases, such as lung cancer.

In accordance with illustrated embodiments set forth herein, described is a device and method for diagnostic analysis of exhaled VBs, and those emitted from tissue and or biological samples for reliable, low cost, and non-invasive health care use.

BRIEF DESCRIPTION OF THE DRAWINGS

The accompanying appendices and/or drawings illustrate various non-limiting, example, inventive aspects in accordance with the present disclosure:

FIGS. 12A-12F illustrate a user interface provided by the computer device/system described herein as well as various settings, options and guidance provided to the user via the user interface.

DETAILED DESCRIPTION OF CERTAIN EMBODIMENTS

Figure 1:
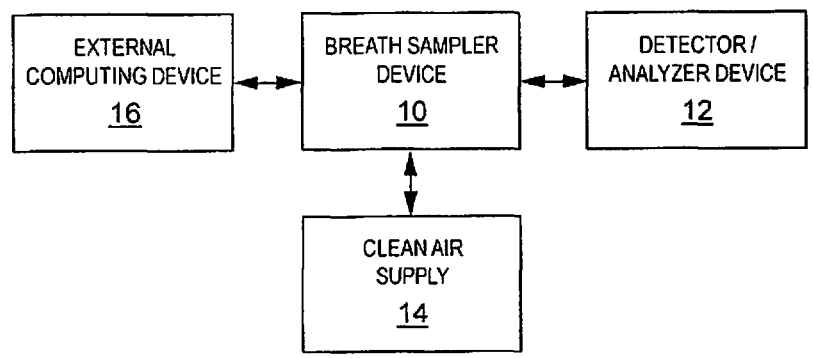
FIG. 1 illustrates a system level overview of an embodiment of a system useful for performing the method of the present invention.

The illustrated embodiments are now described more fully with reference to the accompanying drawings wherein like reference numerals identify similar structural/functional features. The illustrated embodiments are not limited in any way to what is illustrated as the illustrated embodiments described below are merely exemplary, which can be embodied in various forms, as appreciated by one skilled in the art. Therefore, it is to be understood that any structural and functional details disclosed herein are not to be interpreted as limiting, but merely as a basis for the claims and as a representation for teaching one skilled in the art to variously employ the discussed embodiments. Furthermore, the terms and phrases used herein are not intended to be limiting but rather to provide an understandable description of the illustrated embodiments.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the illustrated embodiments, exemplary methods and materials are now described.

It must be noted that as used herein and in the appended claims, the singular forms "a", "an," and "the" include plural referents unless the context clearly dictates otherwise. Thus, for example, reference to "a stimulus" includes a plurality of such stimuli and reference to "the signal" includes reference to one or more signals and equivalents thereof known to those skilled in the art, and so forth.

It is to be appreciated the illustrated embodiments discussed below are preferably a software algorithm, program or code residing on computer useable medium having control logic for enabling execution on a machine having a computer processor. The machine typically includes memory storage configured to provide output from execution of the computer algorithm or program.

As used herein, the term "software" is meant to be synonymous with any code or program that can be in a processor of a host computer, regardless of whether the implementation is in hardware, firmware or as a software computer product available on a disc, a memory storage device, or for download from a remote machine or run in the cloud. The embodiments described herein include such software to implement the equations, relationships and algorithms described above. One skilled in the art will appreciate further features and advantages of the illustrated embodiments based on the above-described embodiments. Accordingly, the illustrated embodiments are not to be limited by what has been particularly shown and described, except as indicated by the appended claims.

Breath VBs analysis is a non-invasive procedure. Breath tests are potentially more sensitive than blood tests because the quantity of collected analysis is limited only by the capacity of the breath collection apparatus and the patience of the donor. As such breath VB analysis allows analysis of the metabolic fraction of a large fraction of blood.

What is described below, and in accordance with one or more illustrative embodiments, is a breath sampler device (e.g. device 10 shown in the below described figures) configured and functional to capture a plurality (e.g., four (4)) samples of the Volatile Biomarkers (VBs) in a patient's in or expired air for later in vitro analysis in a separate laboratory environment (e.g., device 12). It is also to be appreciated the breath sampler device 10 in accordance with one or more illustrated embodiments may be further configured to capture the same and/or different portions of breath to different collection vessels and/or capture media during the same breathing routine. "Media" is to be understood to mean a material to trap the volatile compounds of interest. In some embodiments the media is in a vessel (e.g. the cylindrical tube) but in at least one case the media is outside a vessel (on a fiber that extends into the air flow).

The breath sampler is designed and functional not to cause an unacceptable hazard to the patient or to the clinical staff using it. The electronics and/or software utilized in the sampler device 10 also does not interfere with the patient's vital bodily functions (e.g. breathing). Firstly the sampling mask does not impose any increased breathing resistance. The incorporated pressure and $CO_2$ sensor allow tracing of breathing frequency and efficacy. The operator and/or end-user can program an alarm to sound if hyper/hypo-ventilation or hypo-/hyper-capnia occurs.

The breath sampler device 10 is also configured and functional to be comfortable for the patient while enabling them to breathe either through their mouth and/or through their nose. Additionally, the breath sampler device 10 is designed and configured such that any components of it that are reusable do not come in contact with any biological contamination (bacteria or viruses) in the patient's breath. Further, it is to be appreciated that the breath sampler device 10 is designed and configured to accept a supply of clean air (e.g., from a clean air supply 14) such that any VBs present in the ambient room air are not captured by the device 10. The clean air supply is designed to provide a positive end expiratory pressure for the subject facilitating usage in patients with obstructive and restrictive lung disease. Furthermore, device 10 operates if this supply of clean air has additional oxygen added, up to and including 100% oxygen. This opens the device to use in patients requiring ventilatory support and usage in exposure experiments with spiked gases inhaled by the subjects such as common in diffusion tests. The materials of the breath sampler device 10 preferably do not emit any VBs that would affect the later in vitro analysis into the collected breath. In accordance with a preferred embodiment, the breath sampler device 10 captures up to four separate samples of the VBs in the patient's breath, whereafter each sample is readily and accurately identifiable to ensure that it is simple to track from which patient it came.

With regards to captured breath samples, the breath sampler device 10 is preferably configurable by the user to select the following for each pair of breath VOC samples: a) the portion of in or expired breath to be sampled (e.g. inspired air, oral air, alveolar breath, bronchiolar breath or total breath); and b) the volume of breath to be sampled for each of these fractions In accordance with a preferred embodiment, the breath sampler device 10 commences breath collection within a predetermined period of time (e.g., 30 seconds) of the patient breathing through it while recording its configuration and designated sensor and actuator readings during breath collection, which is preferably recorded to a central database including any warnings or errors that were generated during the breath collection process. During this initial time period the environmental VOCs are washed out. The breath sampler device 10 also preferably provides a User Interface via a display unit to guide a device user through the breath collection process, confirm the results of the collection, and provide any warning messages.

In accordance with the illustrated embodiments described herein, device 10 is preferably programmable to collect breath from a predetermined portion of in- or expired air in a patient's ventilatory system including nasopharynx, oropharynx, bronchi and alveoli. It is to be understood this is particularly advantageous because specific metabolic processes affect VBs differently in different portions of the breath. For instance, diseases in the alveoli leave VOCs in the last portion of breath exhaled by the patient whereas disease in the bronchioles leave VOCs in breath that is exhaled earlier in the exhalation. Furthermore this allows assessment of inspired air to quantify environmental exposures or standardised provocation and exposure experiments.

The breath sampler device 10 described herein is preferably readily assembled and disassembled, preferably without the use of tools (or specialty tools) and is designed and configured such any components that are reusable do not come in contact with any biological contamination (microorganisms) in the patient's breath (with the exception being the sample collection tubes 20, in that after a breath collection, the tubes 20 are returned to a laboratory environment where they are fully recycled and cleaned after analysis).

The captured breath samples are preferably shipped for analysis in suitable protective packaging such that the breath samples captured in the tubes 20 do not require refrigeration or freezing during a shipping process.

In accordance with the described illustrated embodiments (and as mentioned above), the breath sampler device 10 is configured and functional to capture a plurality of patient breath samples (e.g., 1 to 4). Preferably, two independent sample controls are captured, each one able to gather up to two samples in parallel with each other. For instance, for each sample control, the breath sampler device 10 preferably enables the user to configure which part of the breath to collect as follows: 1) how many samples are being collected (0, 1 or 2); 2) whether to use $CO_2$ or pressure to control the collection; 3) whether to start a collection pump when the control sensor reading is rising or falling; 4) the percentage sensor reading threshold at which to start the collection; 5) whether to stop the pump when the control sensor reading is rising or falling; 6) the percentage sensor reading threshold at which to stop the collection; and 7) the volume of breath to be collected.

The breath sampler device 10 is preferably configured and functional such that it records the volume collected in each sample tube (e.g., sorbent tube 20) and stops the collection at the end of the collection event in which the required volume is reached. For instance, when the breath sampler device 10 is collecting two samples on one sampling channel, the collected breath sample volume is split evenly between the two samples in respective tubes. In accordance with a preferred embodiment, the breath sampler device 10 is preferably preconfigured with settings prescribing, and controlling operation of the device 10 to capture one of alveolar breath, bronchial breath and whole breath.

The device or system may comprise one or more of the following:
- GC-FAIMS heated zone to minimize condensing at end of column
- Splits and purge for breath samples to deal with moisture
- Set up of cold trap above freezing to deal with moisture
- Selection of the Tenax/Carbotrap sorbent to cover the range of chemicals that we expect to find in breath while ensuring that both sorbents are hydrophobic so that they repel the high level of water vapour found in breath.
- Rationale for collecting multiple breath fractions
- Potential to collect inspired air for exposure assessment
- Potential to collect inspired air for correction against environmental VBs
- Potential to collect volatile biomarkers originating from micro-organisms
- Potential to use air supply to load inhaled air with components to perform wash-out and/or exposure experiments.

Selective Breath Capture Features
- Use of a pressure sensor and $CO_2$ sensor in the device to track the patient's breathing pattern.
- Use these algorithms to be able to select breath from a particular portion of the air from the respiratory system—examples of this include total breath, total breath but without mouth air, just air from the upper airway, just breath from the lower airway, combined breath from the upper and lower airways, air from the oropharynx and nasopharynx as well as air coming from the stomach.
- Sampling air from one part of the lung is important to localise the breath from the area of the lung that is generating the VOCs.
- Sampling different parts of the breath in order to provide a control which can be used to eliminate exogenous peaks
- Sampling parts of the breath which exclude the volume from the mouth in order to reduce exogenous peaks
- Using pumps based on high frequency piezo technology which can be switched on and off fast enough to sample a part of breath
- Using fixed flow resistance apertures to reduce the effect of variation in sampling tube resistance
- Sampling the inhaled air in order to correct for exogenous compounds
- Create a detailed log file of all the data collected during the breath collection for later analysis to check that the breath collection was valid.
- Use a plurality of separate sampling channels (e.g., two) so that different portions of the same patient's breath can be compared and the differences between the two samples and their similarities can be used in disease diagnosis.
- Have the ability to run zero, one, two (or more) sorbent tubes on each pump so that a wide range of use cases can be covered. This includes the ability to analyse the samples from each sample type on both MS-FAIMS and GC-MS.

Calculating Thresholds
- Monitoring pressure to calculate the point in a breath that originates in a particular part of the lung in order to trigger a pump activation
- Using the first or second differential of the pressure to calculate the point in a breath that originates in a particular part of the lung in order to trigger a pump activation
- Scaling the pressure or differential pressure thresholds according the breathing pattern of a particular patient
- Using a user definable offsets on the learned thresholds to enable a small amount of overlap in sections of breath to be applied
- Scaling any user definable offsets with the magnitude of the breathing so they behave the same across different patients
- Using a number of previous breaths to actively change the calculated points over time to account for changes in the patient's breathing over time
- Applying filters or trimming outliers to learnt breath data in order to exclude anomalous breathing patterns (e.g. talking, coughing or sudden intakes of breaths) before using the pressure or first differential of the pressure to calculate the thresholds
- Applying a running window of a fixed number of the most recent breaths to account for long term trends when sampling (patient relaxing and getting used to the sampling)
- Using hard limits on the time an individual breath is sampled for and the pressure difference across a breath to minimise the effect of an anomalous breathing pattern
- Using $CO_2$ to calculate the point in a breath that originates in a particular part of the lung in order to trigger a pump activation
- Using the point of maximum $CO_2$ to identify a particular part of the lung in order to trigger a pump activation
- Using the pressure at the point of maximum $CO_2$ as the trigger for a pump activation
- If the $CO_2$ is lagging the breath due to its response time calculating the lag and using to find the correct pressure at the point of maximum $CO_2$ If the $CO_2$ is lagging the breath due to its response time using the end of the breath to calculate the lag and using this to find the correct pressure at the point of maximum $CO_2$ Monitoring the patient's breathing rate and providing feedback to the user of the software in order to optimise the breath collection Monitoring the pressure in the mask in order to detect a poorly fit mask and providing feedback to the user of the software if detected Compare the pressure drop inside the system to generate a particular flow rate to expected pump behaviour over time in order to detect a system leak or pump failure Patient Safety Monitoring The $CO_2$ sensor can be used to monitor the adequacy of the patients breathing and set appropriate thresholds to abort sampling procedure in the case of hyper or hypocapnia.

The pressure sensor can be used to monitor breathing frequency and set appropriate thresholds to abort sampling in the case of hypo or hyperventilation.

The air supply of the apparatus can be used to provide the patient with additional oxygen during sampling if medically indicated.

FAIMS Sensor Technology for Detecting VOCs

Using a cold trap that uses the same sorbents as the sampling tubes to ensure that it accurately captures the VOCs found in the tube.

Holding the cold trap at a temperature above freezing so that water does not freeze on the cold trap.

Splitting the sample to only pass some of it through the analytical instrument to reduce the impact of water damage and to avoid overloading the instrument.

Load internal standards onto the sorbent tubes or onto the cold trap to enable internal QC check on the analytical measurement.

Use of a non-polar GC column to reduce interaction with water in the stationary phase and to provide a more robust method when running high volumes of samples.

Correction of retention times through the GC column by regularly testing known QC mixtures on sorbent tubes between running the breath samples and then measuring the time taken for these QC compounds to pass through the GC column and using this to correct the data from later breath samples.

Because a FAIMS system (e.g., such as one manufactured and distributed by Owlstone Inc.) can scan very quickly then continuously scan multiple DF values while the breath sample is passing through the GC column to improve the resolution of the analytes. Use the additional separation available from the FAIMS system to separate VOCs that take the same time to pass through the GC column.

Running FAIMS at high temperature to prevent water and other compounds condensing at the FAIMS entrance. This improves the quality of the resulting spectra and prevents damage to the GC column.

Run breath samples on both the GC-FAIMS and the GC-MS and combine the data from both platforms to generate the cancer classifier. It is to be appreciated this is advantageous because there are some VOCs where the GC-FAIMS is better at detecting them and some where the GC-MS is better.

Check the system by running a homologous series of compounds through to check both the GC retention times and the FAIMS performance. This is particularly important as the FAIMS can operate at a wide range of temperatures.

Complete in Place Solutions

Drawing a section of breath onto a cold trap in order to concentrate the sample before measurement on a DMS system Drawing different sections of breath onto a number of cold traps in order to concentrate the sample before measurement on a DMS system in sequence (as well as samples of breath drawing in ambient air onto a trap in order to eliminate exogenous compounds)

Using a micro GC or short air compatible GC on a DMS system to provide basic pre-separation Running at low temperature isothermal GC conditions to prevent degradation of breath compounds Using a metal-organic framework as a sorbent to allow air to be used as the carrier gas Re-collecting sample and repeating with different thermal desorption profile or GC temperature to provide additional separation Running recollected samples if certain peak/feature/pattern is observed—optimise for fast negative (all clear) method Combining with a NDIR/FTIR measurement to provide additional chemical information Sampling directly onto a DMS system and using Acetone or other high intensity compound as the marker of the section of breath. Using the DMS as the selector for the part of breath and loading a cold trap or sorbent tube. When the collection is complete, desorb the pre-concentrated sample back into the DMS Turning now descriptively to the drawings, in which similar reference characters denote similar elements throughout the several views, FIG. 1 depicts a system for collection of volatile biomarkers, or other animal body, includes a vapor sampling device 10 and a separate detector/analyzer apparatus 12, a clean air supply source 14 and external computing device 16 to be coupled to device 10. It is to be appreciated that for ease of description purposes, the illustrated embodiments described herein are discussed in reference to a vapor sampling device 10, such as a breath sampler, for collecting breath samples from a human patient to collect volatile biomarkers for biomedical purposes. However, the illustrated embodiments are not to be understood to be limited thereto as they may encompass vapor sampling devices for capturing other vapors from a body such as those that emit from stool and urine, as could be of interest for detecting the presence of colon cancer and prostate cancer. Additionally, while FIG. 1 depicts the vapor sampling device 10, detector/analyzer apparatus 12, the clean air supply source 14 and external computing device 16 as separate units, the illustrated embodiments are not to be understood to be limited thereto as they also may encompass a device 10 that incorporates one or more the aforesaid ancillary components.

Figure 2A:
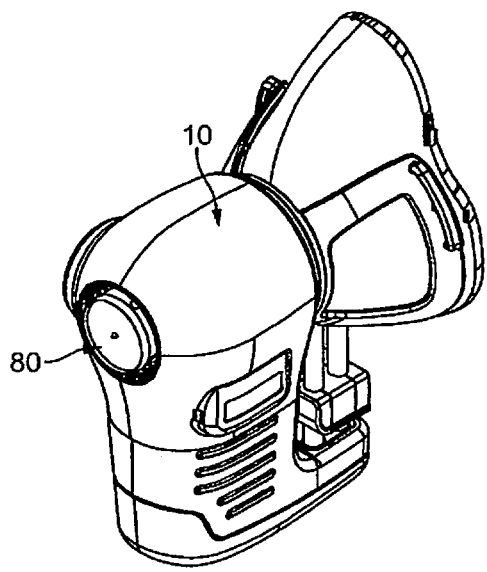
FIGS. 2A and 2B illustrate a perspective (FIG. 2A) and cross-sectional view (FIG. 2B) of an embodiment of a breath sampler device of use in performing the method of the present invention.
Figure 2B:
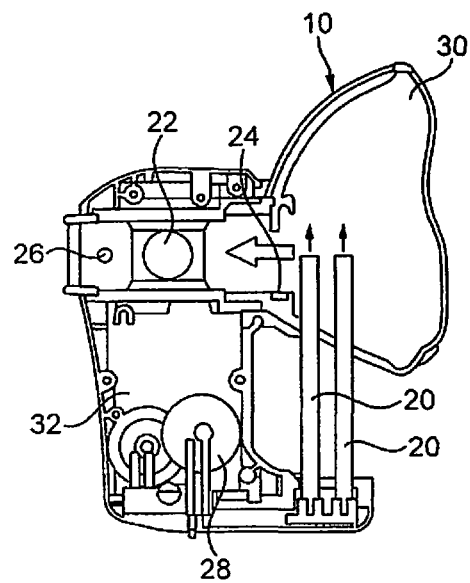
Figure 5:
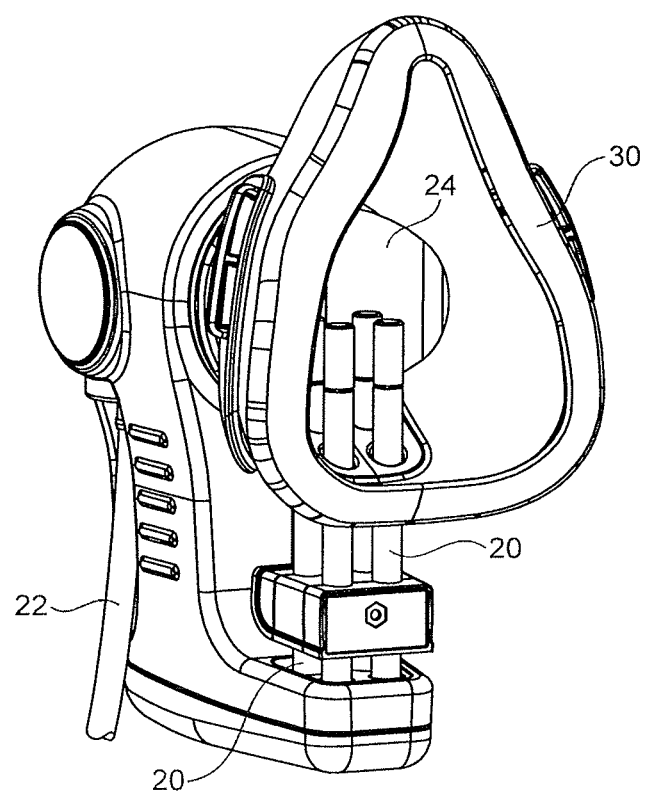
FIGS. 5-7 illustrate various perspective view of the device of FIGS. 2A and 2B.
Figure 6:
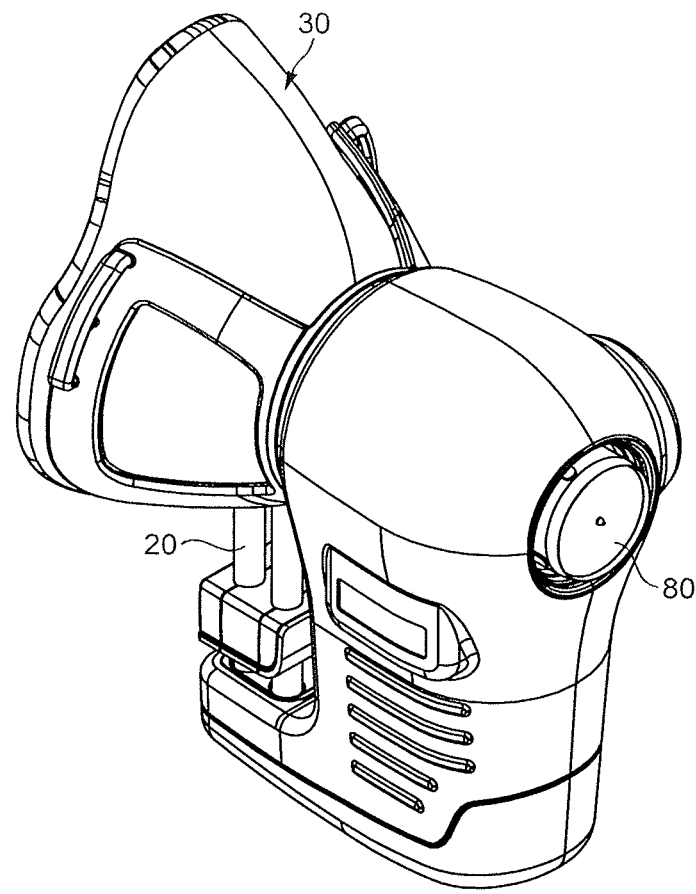
Figure 7:
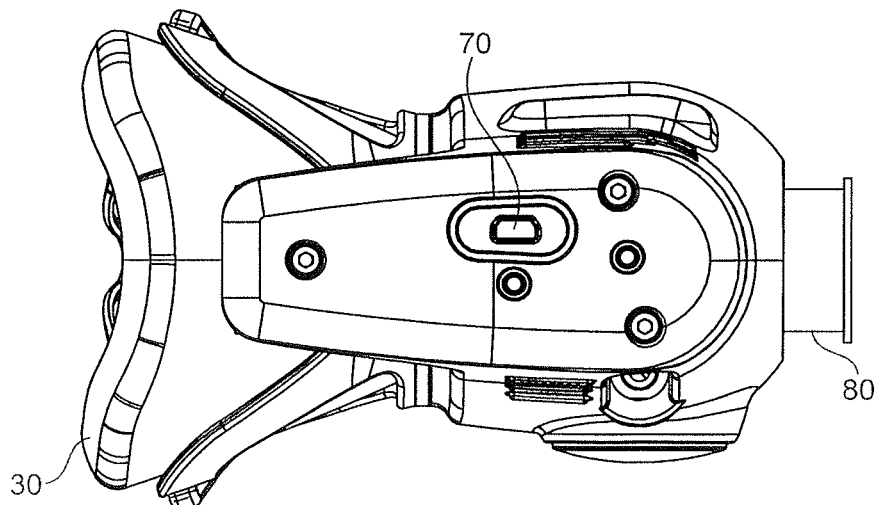

With simultaneous reference to FIGS. 2A and 2B, depicted is an illustrative embodiment of a breath sampling device 10 (FIG. 2A) and its cross-sectional view (FIG. 2B). Additionally views of the device 10 are also shown in FIGS. 5-7.

What is described below is a vapor sample (e.g., a breath sample), obtained from the patient via the breath sampling device 10, which is then captured and held in sorbent tubes 20. The sorbent tubes 20 are subsequently removed from the breath sampling device 10 and disposed within a detector/analyzer apparatus 12, which is functional to extract the breath sample from the sorbent tube 20 so as to preferably perform a FAIMs analysis thereon to detect VBs in the breath sample to diagnosis lung cancer. It is to be understood device 10 in FIGS. 2A and 2B depicts two (2) sorbent tubes, but it is to be appreciated device 10 may be configured to accommodate any desirable number of sorbent tubes 20.

Figure 9A:
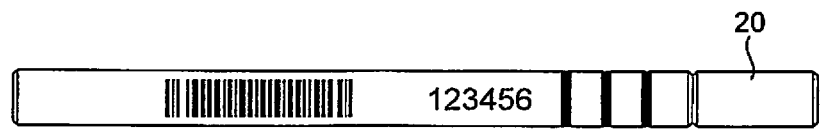
FIG. 9A illustrates a perspective view of a sorbent tube used with the device of FIGS. 2A and 2B.
Figure 9B:
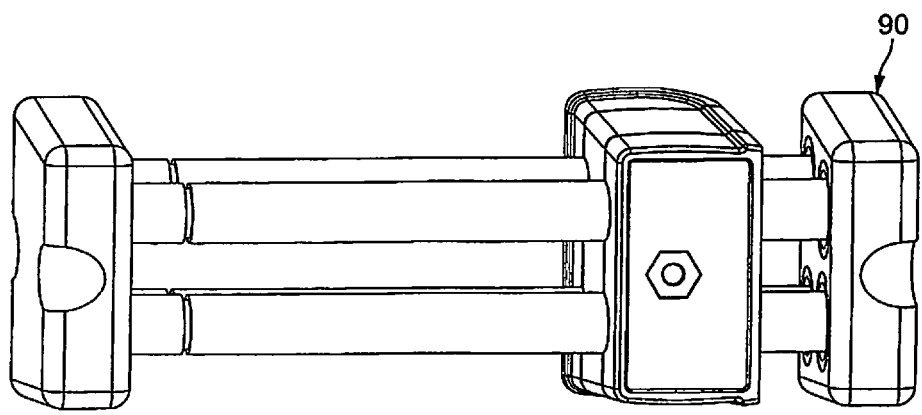
FIG. 9B illustrates a packaging container used to transport the sorbent tube used with the device of FIGS. 2A and 2B.

As mentioned above, the device 10 collects VBs in sorbent tubes 20 (FIG. 9A). For instance, a sorbent tube 20 used with device 10 is preferably a stainless steel tube which is approximately 3 inches long and has a ¼ inch diameter containing a sorbent material (e.g., similar to activated carbon) that is specifically designed to absorb VBs and to then re-emit them when the tube 20 is preferably heated in detector/analyzer apparatus 12. It is to be appreciated the tubes 20 can be stored for several days and can be shipped via mail and package carriers via preferably a packaging container 40 (FIG. 9B). It is to be understood the sorbent tubes 20 are preferably glass coated stainless steel tubes packed with absorbent resins (sorbents) designed to trap VBs. When the tubes are subsequently heated in a laboratory environment 12, they release the VBs allowing them to be analyzed. As shown in FIGS. 2A, 2B, 5 and 6, the sorbent tubes 20 preferably push through holes formed in the mask 30 and then connect into the device frame at the bottom portion of the device 10. The sorbent tubes 20 are preferably held via a clamp device to simplify installation and removal from device 10. The sorbent tubes 20 are preferably mounted unevenly (e.g., 12 mm spacing at a front portion and 14 mm at a back portion of device 10) so that the block of the sorbent tubes 20 will only fit into the breath capture unit via a designed orientation.

For instance, the sorbent tubes 20 are each preferably hollow glass passivated stainless steel tubes dimensioned to be 89 mm long by 6.4 mm (3.5" by ¼") OD packed with Tenax GR and Carbograph 5TD, which is the sorbent mix adapted to trap VOCs from a patient's breath. After a breath sample is collected in the tubes 20, they are then sealed and removed from device 10 for subsequent analysis in analytical/detection device 12 (whereafter the tubes 20 are preferably heated to release the VOCs into the analytical instrument 12). It is to be understood sorbent material is retained at each end of the tube 20 by glass wadding and tightly fitting stainless steel gauze at each end of the tube 20. This ensures that the sorbent material cannot escape from the tube 20. With reference to FIG. 9A, each sorbent tube 20 is preferably labelled with a unique serial number and bar code for easy identification and an arrow indicator is preferably provided to show the direction of breath flow. Also shown in FIG. 9B is a packaging transport device 40 used to transport tubes 20 removed from the breath sample device 10 to a remotely located analytical/detection device 12 preferably in a laboratory environment.

With regards to construction and assembly of device 10, it preferably includes a $CO_2$ and pressure sensor 22, replaceable bacterial filter 24, clean air supply 26, pump(s) 28, a replaceable flexible face mask 30 and a control board 32 for controlling operation of the aforesaid primary components of device 10. The functionality of the aforesaid primary components are further discussed below, and the control board 32 is to be understood to include one or more of the system components shown in FIG. 11 (as also described below).

During a tidal breathing procedure, the $CO_2$ and pressure sensor 22 preferably monitors breathing adequacy and frequency while pump(s) 28 facilitate passage, and capture, of a portion of a patient's breath in the sorbent tubes 20. The sensor 22 is further preferably configured to measure pressure and temperature within the mask 30 as well as $CO_2$ level in the mask 30. For instance, the sensor 22 may include a $CO_2$ sensor 22 component (e.g., such as a readily available Sprint™ IR-W-X type sensor for measuring/detecting a level of $CO_2$) in the mask 30, which may be optionally used for selecting a portion of the patient's breath the device 10 collects in sorbent tubes 20 (as described herein).

In accordance with an illustrated embodiment, the pressure sensor component of sensor 22 may be a readily available Bosch™ BMP280 combined pressure temperature sensor configured and functional to monitor the pressure in the mask 30, which as described herein is utilized for selecting a predetermined portion of a patient's breath to capture (via the sorbent tubes 20). Preferably, device 10 contains six absolute pressure temperature sensors 22. For instance, sensor 22 is mounted preferably in the mask 30 to measure the pressure and temperature of the patient's breath. Another sensor 22 is preferably mounted on the inlet and on the outlet of each pump 28 and the other sensor(s) to monitor ambient pressure and temperature regarding the device 10. For instance, the aforesaid sensors 22 are utilized such that the mask pressure sensor 22 measures the pressure in the mask, which is utilized to determine the correct points to switch on and off the collection pumps 28 to collect a designated portion of the patient's breath (e.g. alveolar) for capture in the sorbent tubes 20. The $CO_2$ sensor 22 measures the $CO_2$ level in the patient's breath and is an alternative to pressure for the pump control. It is noted that the difference between the mask pressure sensor and the pump inlet pressure sensor is preferably utilized to detect leaks and blockages in the sorbent tube 20 and associated air passageways, and to detect if a sorbent tube 20 is not properly fitted in device 10. It is further to be understood that the difference between the pump inlet pressure and the pump outlet pressure is also utilized to determine if a pump 28 is working properly, to check for blockages or leaks, and to measure the flow rate through each pump 28. The flow rate is integrated to determine the amount of breath collected from a patient. It is additionally to be further understood that the difference between the pump outlet pressure and ambient pressure may also be used to determine if a pump outlet is blocked.

In accordance with a preferred embodiment of the present invention, the sensors 22 have the following specifications:

| Parameter | Value | Notes |
|---|---|---|
| Pressure range | 300-1,100 mBar | |
| Absolute Accuracy | ±1.0 mBar | Over 950-1,050 hPa |
| Relative accuracy | ±0.12 mBar | |
| Temperature Range | −40 to +85° C. | |
| Pressure Resolution | 0.01 mBar | |
| Temperature Resolution | 0.1° C. | |
| Measurement Rate (slowest mode) | 23.1 Hz | Worst Case |

It is to be understood that the output of the aforesaid sensors 22 is preferably digital such that full measurement specification may be provided to the aforesaid software executing on the external computing device 16.

During testing of a preferred embodiment of the device 10, it was determined the pressure range in the mask 30 was typically ±500 Pa (±5 mBar) either side of atmospheric. To control the sampling accuracy when using pressure as the input, the breath sampler device 10 is preferably configured and functional to establish the maximum and minimum pressure in each breathing cycle, and then be able to resolve the maximum and minimum pressure in each breathing cycle. In operation the following specifications for mask pressure measurement is preferably:

Measurement Range: 790-1,100 mBar
Relative Accuracy: ±100 Pa (±1 mBar)
Resolution: 10 Pa (±0.1 mBar)

It is to be appreciated 790 mBar is the expected atmospheric pressure at the highest city in Europe and America (Santa Fe, N. Mex. 2,213 m). The highest atmospheric pressure ever measured on earth is 1083 mBar (Agata, Siberia, Russia Dec. 31, 1968). Thus, it is to be understood the relative accuracy is the accuracy with which the mask pressure sensor 22 can measure the difference between the pressure in the mask 30 and the pressure in the room (as measured by the environmental pressure sensor) once the offset between the two has been corrected for (if required), preferably with the mask 30 not fitted to the patient and the external air supply 14 switched off.

With regards to the $CO_2$ sensor 22, illustrative specifications include:

| Parameter | Value |
| --- | --- |
| Measurement Range | 0-20% $CO_2$ |
| Absolute Accuracy | ±70 ppm ±5% of reading |
| Temperature Range | 0 to +50° C. |
| Operating Pressure Range | 950 mbar to 10 bar |
| Measurement Rate | 20 Hz |
| Resolution | 0.0001% |

It is noted the output of the $CO_2$ sensor 22 is preferably in ppm such that known conversion factors are required to convert acquired data to percent $CO_2$. It is also noted that a requirement for $CO_2$ sensing is that the device 10 preferably reads mask $CO_2$ in the range 0-10% $CO_2$ at 5 Hz to a minimum resolution of 0.05% and to an overall accuracy of ±0.5% $CO_2$ over the normal breath range of 0-5% $CO_2$. The aforesaid $CO_2$ sensor 22 preferably has a resolution of 0.1 ppm or 10-5% and a "worst case" absolute accuracy of ±70 ppm±5% of 5%=±0.257% $CO_2$.

With regards to $CO_2$ measurement and accuracy, the $CO_2$ concentration is expected to be less than 0.1% in the input air and approximately 4.5% in the exhaled breath. As with pressure to control the sampling accurately when using $CO_2$ as an input, the breath sampler device 10 is preferably configured and functional to establish the minimum and maximum $CO_2$ levels for each breathing cycle and to resolve between the minimum and maximum $CO_2$ levels for each breathing cycle. In a preferred embodiment, the device has a detection rate as follows:

Measurement range: 0-10% (to provide cover for high levels)
Measurement accuracy: ±0.4% $CO_2$ over 0-5% (10% of expected range)
Resolution: 0.04% $CO_2$ (one percent of the expected range)

With regards now to the replaceable bacterial filter 24 and flexible face mask 30, they preferably prevent instances of cross-contamination relative to a patient's breath. The biological filter 24 is preferably mounted in the mask 30 and is configured and constructed to ensure that all biological contamination in the patient's breath (e.g., bacteria or viruses) come in contact with the mask 30 and the filter 24 (both of which are one-time use) and the sorbent tubes 20 (which are preferably baked at around 300° C. before use with each different patient). The face mask 30 is preferably formed of silicone material designed for both patient comfort, and to contact the sorbent tubes 20, the biological filter 24 and a portion of the housing for device 10 (as shown in FIGS. 2A and 2B). It is noted the mask 30 does not obscure a patient's vision while permitting the patient to breathe through their mouth and/or nose.

With further regards to cross-contamination, device 10 is fitted with a clean air supply valve 26 which intakes clean air from an external source 14 so as to avoid contamination of the patient's breath with the ambient air surrounding device 10 and the patient. In the illustrated embodiment of FIGS. 2A and 2B, device 10 is configured to contain a pair of sorbent tubes 20, wherein each sorbent tube 20 may be independently gated to collect different breath fractions during a same breath collection event. It is to be understood the sorbent tubes 20 are to contain patient breath samples which are to be analyzed offline (separate from device 10) on numerous testing platforms, including (but not limited to) GC-MS and GC-FAIMS platforms in a laboratory environment 12. For instance, such platforms may include an ion mobility spectrometer and method as disclosed in commonly assigned U.S. Pat. No. 7,714,278 and a corona ionization device and method as disclosed in commonly assigned U.S. patent publication no. 2014/0299759, both of which are incorporated by reference herein in the entirety.

It is also to be understood, in an alternative embodiment, device 10 may be coupled directly to a detector/analyzer apparatus 12 thus obviating the need to separately remove the sorbent tubes 20. It is to be further appreciated that four calibrated orifice plates may preferably be provided in device 10 to balance the flow through the sorbent tubes 20 (FIG. 7).

With regards to pump(s) 28, it is to be understood two computer controlled pumps 28 are provided in the illustrated embodiment, each configured to draw a patient's breath through the sorbent tubes 20 (e.g., one pump 28 for each pair of tubes 20). Each pump 28 preferably has an absolute pressure sensor mounted directly upstream of it and downstream of it to determine the flow rate through the pump 28 and to detect leaks and blockages (as mentioned above). A microprocessor is preferably provided in the control board 32 to provide a level of control of the pumps 28 and to read sensors and to provide this information over a USB connection 70 (FIG. 7) to preferably an external coupled computing device 16 (FIG. 1) (e.g., such as a desktop, laptop, tablet or computing type device). It is to be appreciated the USB connection 70 further facilitates electrical power delivery to the device 10. It is to be further understood software is preferably executing on the aforementioned external computing device 16 to control data sampling and to record results regarding patient breath samples. It is also to be understood the aforementioned microprocessor 32 is coupled to associated drive electronics configured to operate the pumps 28, read the sensors 22 and communicate such data to the external computing device 16.

As previously mentioned, the device 10 of the illustrated embodiment is preferably controlled by software executing on an external computing device 16. With regards to the software, it is to be understood its execution effects communication via the USB connection 70 with the pumps 28 functional to communicate with and read the sensors provided in the device 10 (e.g., sensors 22); control the pumps 28 to turn on and off at the designated times to collect a selected portion of a patient's breath; track an amount of breath collected in each sorbent tube 20 and stop collection when an ample amount of patient's breath has been collected; and guide an operator/user (e.g., medical professional), preferably via a user display or GUI provide on the external computing device 16 or device 10, through a breath collection process with the provision of appropriate feedback.

With regards to the present illustrated embodiment, it is to be further understood, each pump 28 preferably has a pressure sensor mounted upstream and just downstream of it, which pressure sensors are used to determine the flow rate through the pump 28 and to detect whether the pump 28 and/or a sorbent tube 20 is leaking or blocked. It is to be appreciated the pumps 28 are preferably configured to exhaust to the ambient air surrounding device 10. Additionally, orifice plates (as shown in FIG. 7) having small accurate flow restrictors are provided on the device 10 configured to provide an accurate flow resistance positioning the pumps 28 into a correct portion of their operating curve to mitigate the variation in the flow between the sorbent tubes 20 on the pumps 28 caused by differences in their flow resistance.

Figure 3:
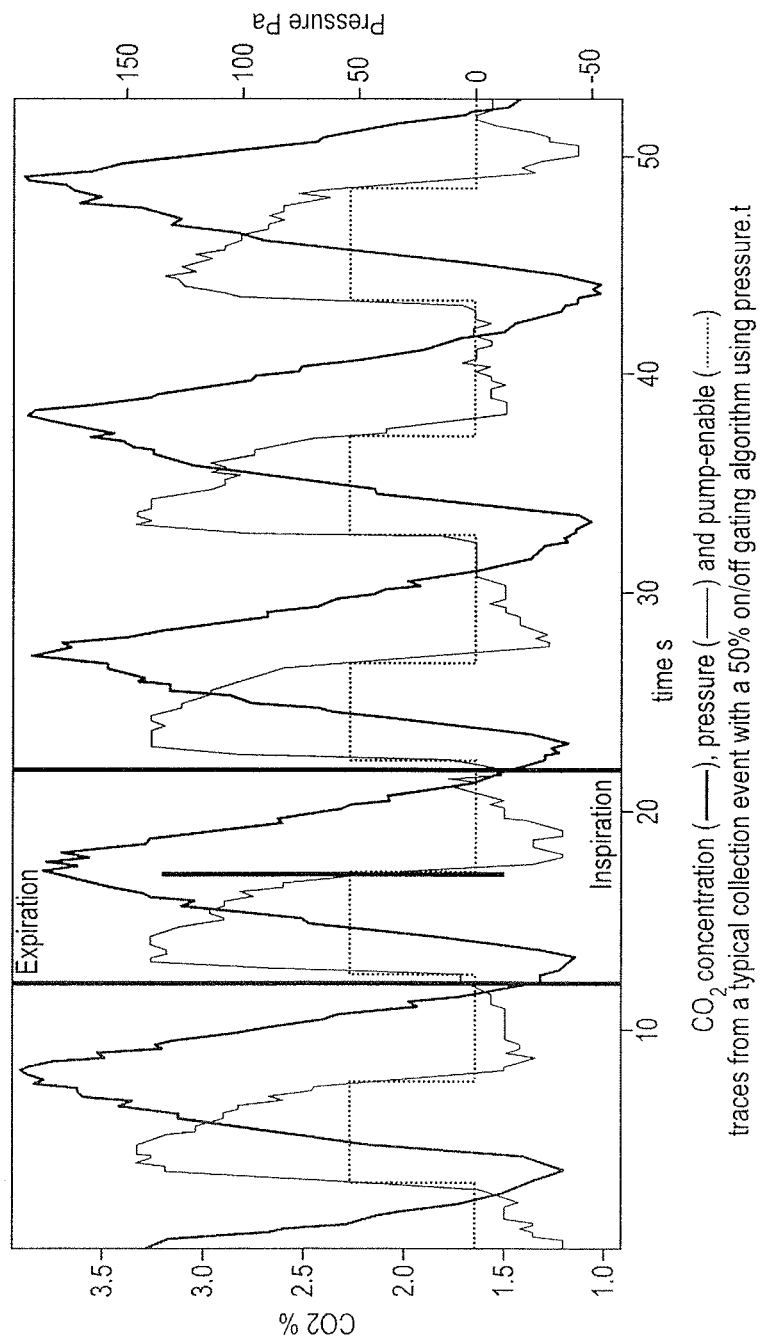
FIG. 3 and FIGS. 4A and 4B depict analysis of test data regarding capture of a patient's breath using the device of FIGS. 2A and 2B and system of FIG. 1.
Figure 4A:
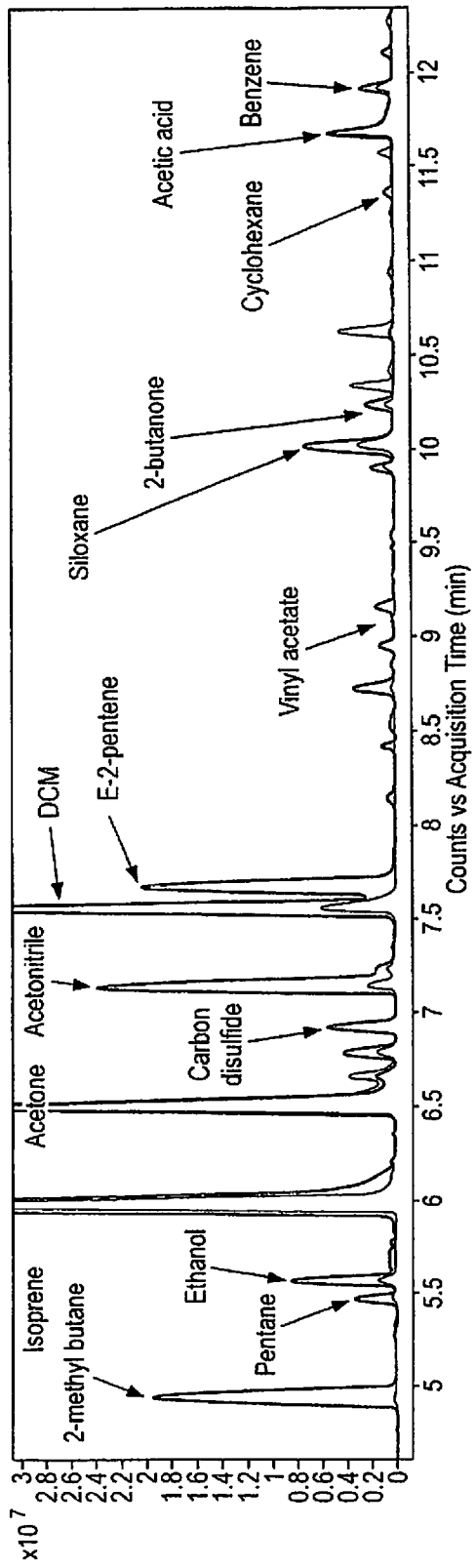
Figure 4B:
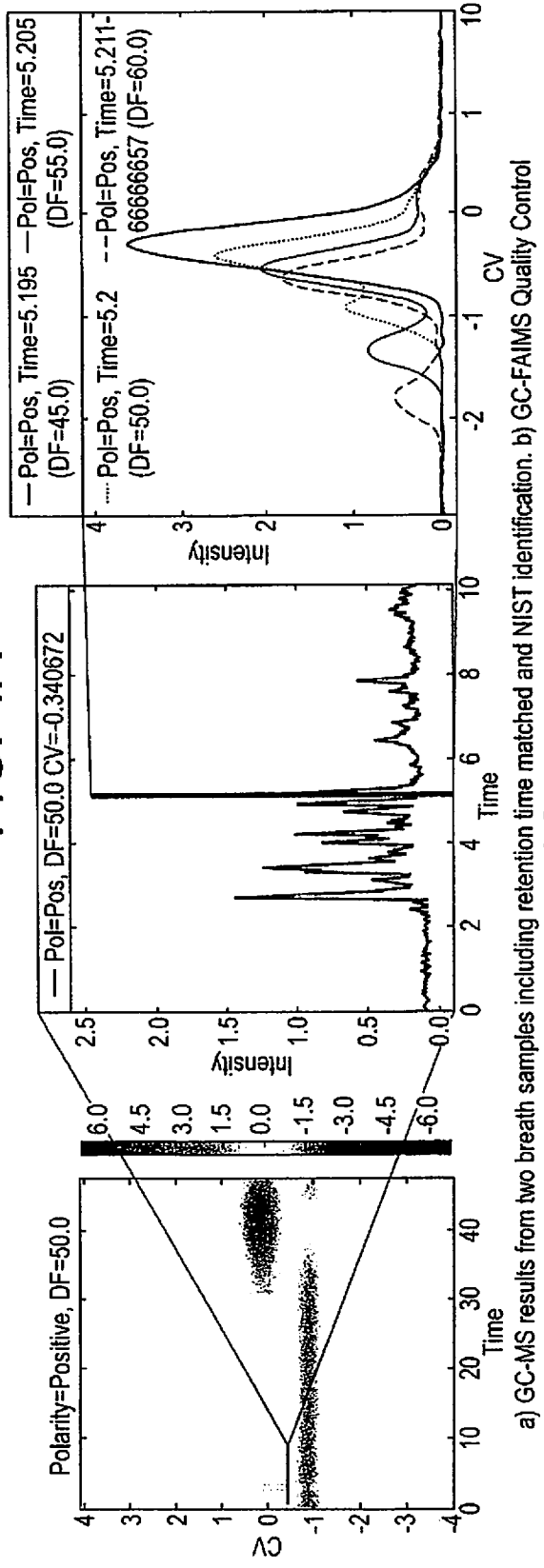

With reference now to FIGS. 3, 4A and 4B, illustrated are actual test result data regarding usage of device 10 with one hundred (100) patients. FIG. 3 illustrates $CO_2$ concentration, pressure and pump-enable traces from a collection event with a 50% on/off gating algorithm using pressure. And FIG. 4A illustrates GC-MS results from breath samples including retention time matched and NIST identification while FIG. 4B illustrates GC-FAIMS quality control.

Figure 8:
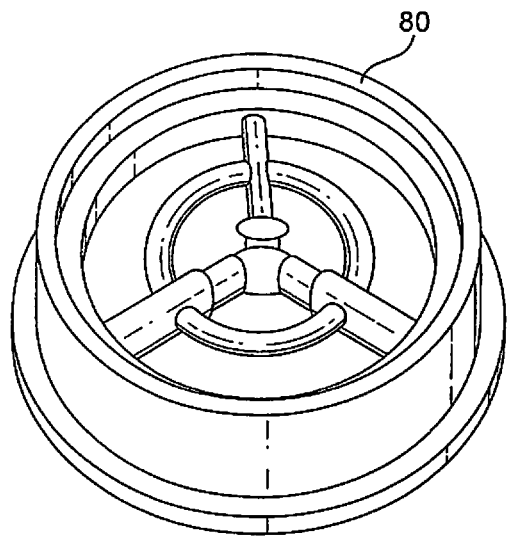
FIG. 8 illustrates a one-way valve used in the device of FIGS. 2A and 2B.

Continuing with operation of the device 10, it is to be understood a patient fits the disposable silicone mask 30 to the patient's face preferably configured to allow them to breathe through their nose and/or mouth. A head strap is preferably fitted to the face mask 30 to hold the unit in place on the patient. The biological filter 24 is preferably provided at the outlet portion of the mask 30 designed to prevent contamination from the patient's breath coming in contact with the breath sampler device 10. As mentioned above, a clean air supply 14 (via valve 26) enables the patient to breath air that is preferably free of VBs that might be present in the ambient room air surrounding device 10, as these would contaminate the breath sample. It is to be understood the outlet portion of the mask 30 includes a one-way valve 80 (FIG. 8) permitting the patient to breathe out to the room while inhaling (scrubbed) clean air, via its coupling to a clean air supply source 14 (via valve 26). It is to be understood the aforementioned one-way valve 80 is preferably a mechanical unit consisting of a plastic membrane that permits air out of the device 10 but does not permit air in.

The breath sampler device 10 preferably starts the collection within a predetermined time from device activation (e.g., 30 seconds) preferably triggered by a patient breathing through it and subsequently confirms to the medical professional attending operation of the device 10 that the collection process is complete. Preferably, a medical professional is able to prescribed a maximum time for the patient breath collection, and if the required volume of breath has not be collected within the prescribed time, collection ceases (e.g., an error message may be displayed). With regards to operation of device 10, FIGS. 12A-12F depict exemplary screen displays provided to a medical professional user (e.g., via external computing device 16) regarding aspects of operation of device 10.

With regards to the breath flow rate through the sorbent tubes 20, it is to be understood if it is too slow the patient then has to spend too long a time breathing into the mask 30, and if the breath flow rate is too fast then the most volatile chemicals are likely lost by not being captured within the sorbent tubes 20. Test data has demonstrated that 200-300 mL/min is an optimum rate through each tube 20 whereby the flow rate generates a pressure drop across the sorbent tube 20 of 42.5 mBar. It is noted that the collected breath volume is a compromise between patient comfort and having enough time to collect VOCs to analyze. In accordance with an illustrated embodiment, 1.2 litres on each tube 20 is optimal, requiring a test length of approximately 6 minutes. It is noted though that the actual collected volume and flow rate may be chosen by a medical professional user of device 10.

Figure 10:
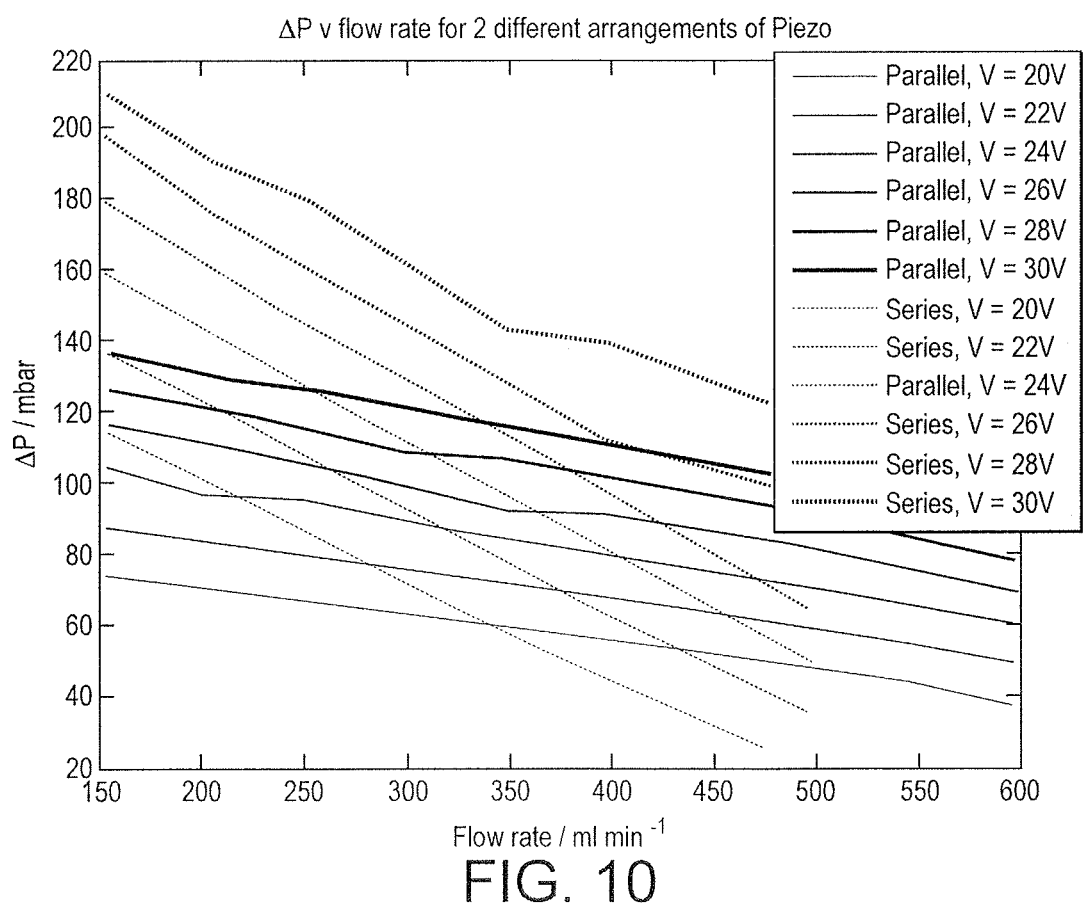
FIG. 10 illustrates a chart depicting data regarding operation of pumps used in the device of FIGS. 2A and 2B.

Regarding operation of the pumps 28, each pump has a flow characteristic as shown in FIG. 10. It is to be appreciated that for optimum collection, the sorbent tubes 20 require a flow rate of up to 300 mL/min each, thus each pump 28 should deliver up to 600 mL/min. Additionally, as shown in the pump flow characteristics of FIG. 10, each pump 28 preferably has two separate pump units that can be plumbed in series or in parallel, wherein the graph depicted in FIG. 10 shows a parallel connection.

With further regards to operation of the breath sampler device 10, it is preferably required to collect 95% of the patient's breath that the medical professional expects and no more than 5% of other breath. As mentioned throughout this description, the portion of a patient's breath is collected and determined by when in each breath cycle the sample collection pump 28 is turned on and off. The accuracy of this is determined by: i) the accuracy of the mask pressure or $CO_2$ measurement; ii) the latency in reading the sensors 22; and iii) the latency in switching the pumps 28 on or off. In operation, typical breathing rates in adults are 16-20 breaths per minute, extending to 10-30 breaths per minute for patient's over 80 years of age. Therefore, in use, the breath sampler device 10 is preferably configured and adapted to operate from 8-30 breaths per minute, corresponding to a breath every 2.0-7.5 seconds. Thus, to satisfy these operating parameters, (95% of the correct breath is preferably collected and only 5% of incorrect) requires a timing accuracy of ±2.5% of a breath for both the start and end of breath collection. Accordingly, execution of the firmware embedded in device 10 requires that: the firmware reads the control sensor (mask pressure or $CO_2$); sends readings to the externally coupled computing device 16 (preferably via USB connection, or wireless connection). And the PC software executing on the externally connected computing device 16 reads the aforesaid captured data to determine the time to switch the state of the pump between on/off, which software also sends a message to the device embedded firmware to execute operation of the pumps 28.

Regarding the breath flow measurement accuracy for device 10, the device is configured and functional to derive the flow rate through each sample collector preferably in the range 0-300 mL/min at 5 Hz with an accuracy of ±5% to meet the requirement that the volume of breath collected is accurate to ±5%. The flow rate is preferably determined by measuring the pressure drop across the pumps 28. The flow accuracy is therefore generated by the accuracy of the pressure measurement and the accuracy of the flow calibration. The approximate total error expected between the two pressure readings (pump upstream and pump downstream) is ±2.0 mBar (as indicated above) which is equivalent to a flow measurement error of ±0.67 mL/min or ±0.34% of the expected flow rate of around 200 mL/min. Thus, it is evident that there is therefore a requirement that the flow characteristics of each system are calibrated accurate to better than ±4.6%.

In operation, the flow path for the breath samples (air) through the sorbent tubes 20 is as follows: first, the collection of breath (air) commences in the mask 30 where there is preferably a pressure sensor (Pmask). The collected air from the patient then goes through the sorbent tubes 20, and then through an orifice plate (FIG. 7). Pressure is measured upstream of the pump 28 (Pup), which passes through the pump 28. The pressure is also measured downstream of the pump (PDown) and then vented to atmosphere. It is to be appreciated that the pressure rise across each pump 28 is a function of the flow through it (as mentioned above) and as a result by comparing the pressure rise across a pump 28 with that expected for the voltage applied it facilities the detection of air blockages in device 10. For example, at 24V the expected pressure rise is around 80 mBar at 500 mL/min (the expected flow), but when blocked, the pressure rise will be 110 mBar. The pressure sensors can measure the pressure rise to ±0.24 mBar. It is noted this same method is used to detect leaks. That is, if there is a leak where a sorbent tube 20 connects to the breath capture unit (e.g., detected by the change in the pressures). Using this process, the differences in the flow resistance of a sorbent tube 20 compared with another tube 20 connected to the same pump 28 is thus evident.

In operation, it is further noted that each tube 20 has a Lee orifice plate in series with it and the pressure drop across these plates balances the flow between the two tubes 20 such that approximately a 10% difference in flow resistance only causes a 4.8% error in the flow in that tube and a 0.9% error in the other tube. Thus, device 10 is configured and functional to detect when the wrong number of sorbent tubes 20 has been fitted as the flow rate will be half (or twice) that is expected, this pressure drop will be incorrect.

Discussion is now provided regarding the process the device 10 performs regarding verification that the patient breath sample it has collected is correct. Preferably, during operation of the device 10, the following device readings are monitored to determine whether they reside within predefined limits: 1) the patient's breathing rate; 2) the $CO_2$ level during exhalation; 3) the pressure during inhalation; and 4) the pressure during exhalation. The device 10 preferably performs a routine that checks that the pumps 28 have been turned on and off correctly throughout the collection and that there are no leaks or blockages in the breath collection path and whether an air blockage present in the sample collection path which would compromise the capture of patient breath samples.

With certain illustrated embodiments described above, it is to be appreciated that various non-limiting embodiments described herein may be used separately, combined or selectively combined for specific applications. Further, some of the various features of the above non-limiting embodiments may be used without the corresponding use of other described features.

Figure 11:
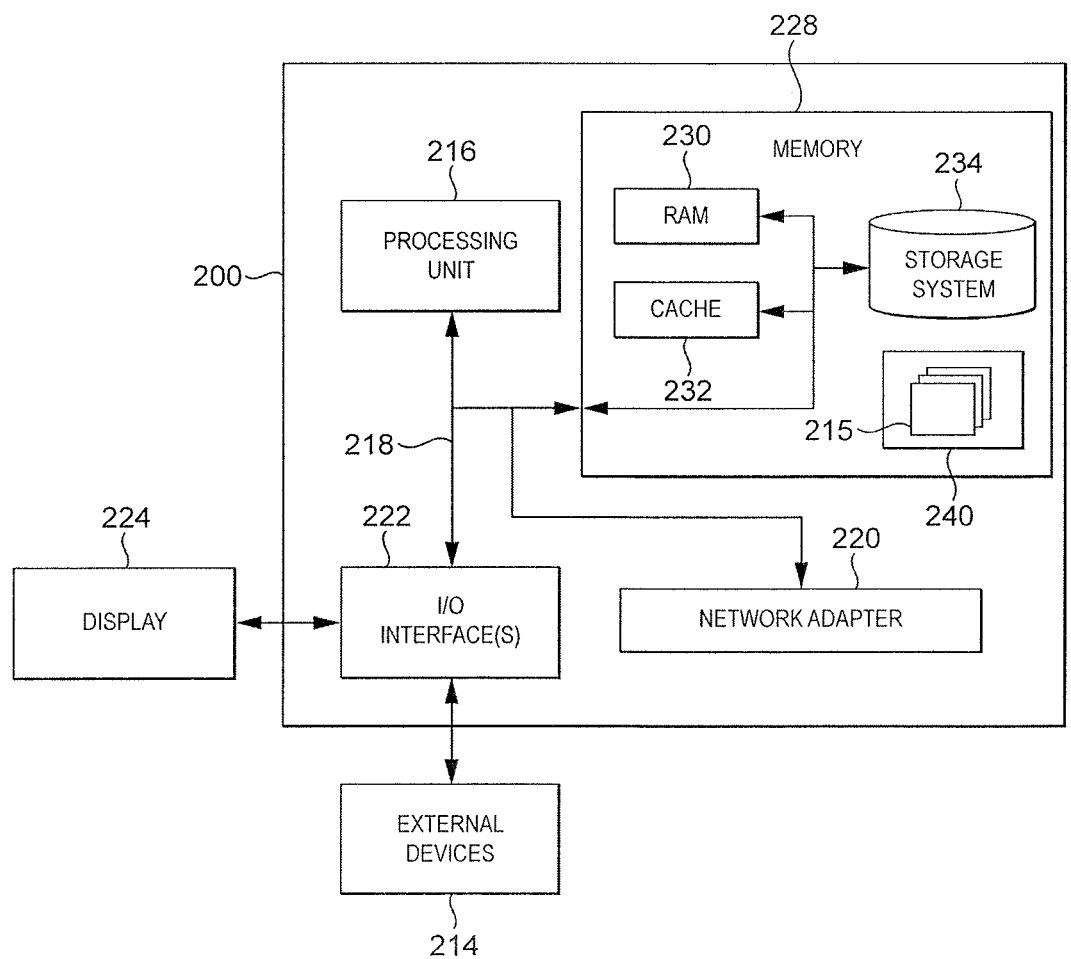
FIG. 11 illustrates an example computer device/system which may be used in the device of FIGS. 2A and 2B.
Figure 12A:
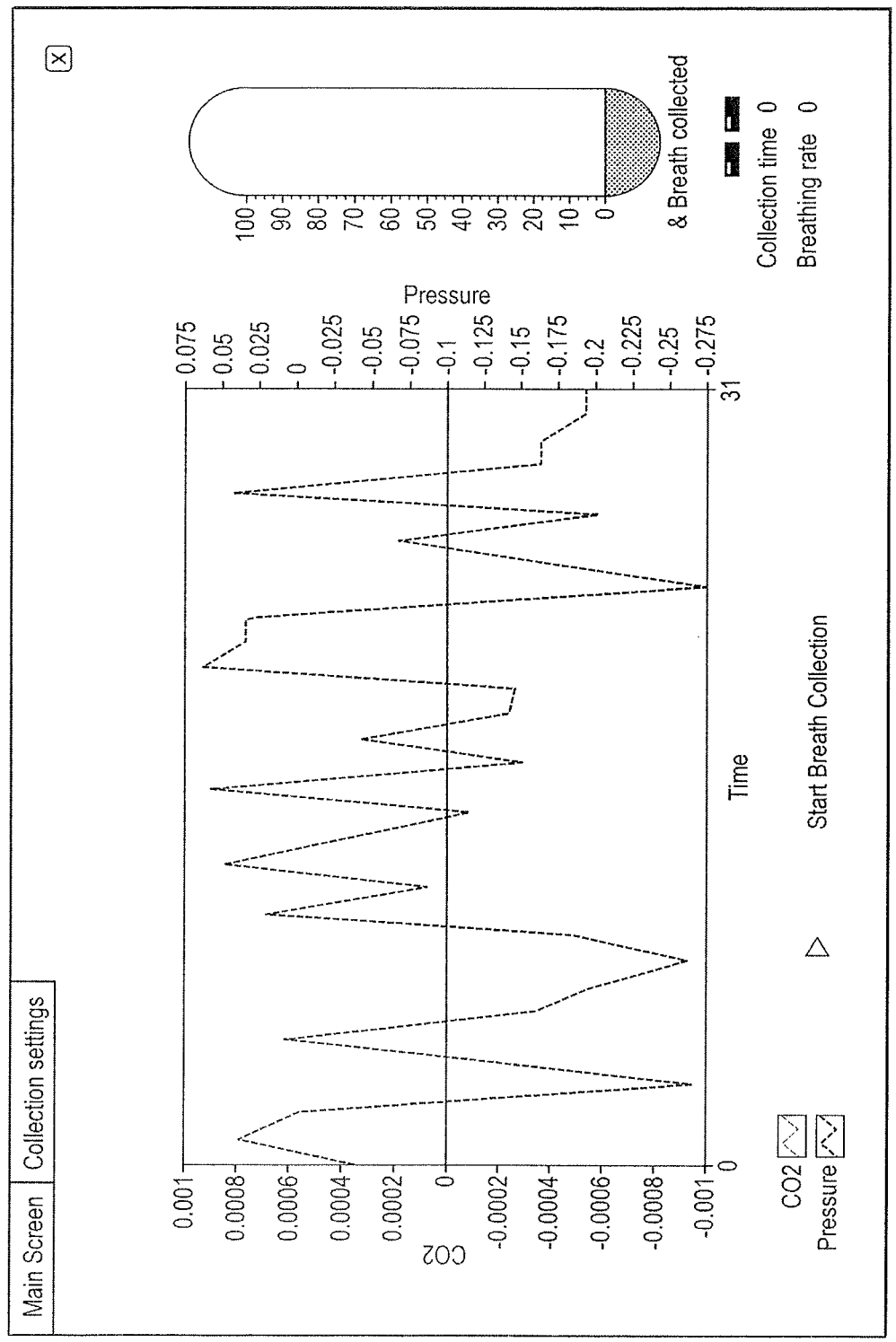
Figure 12B:
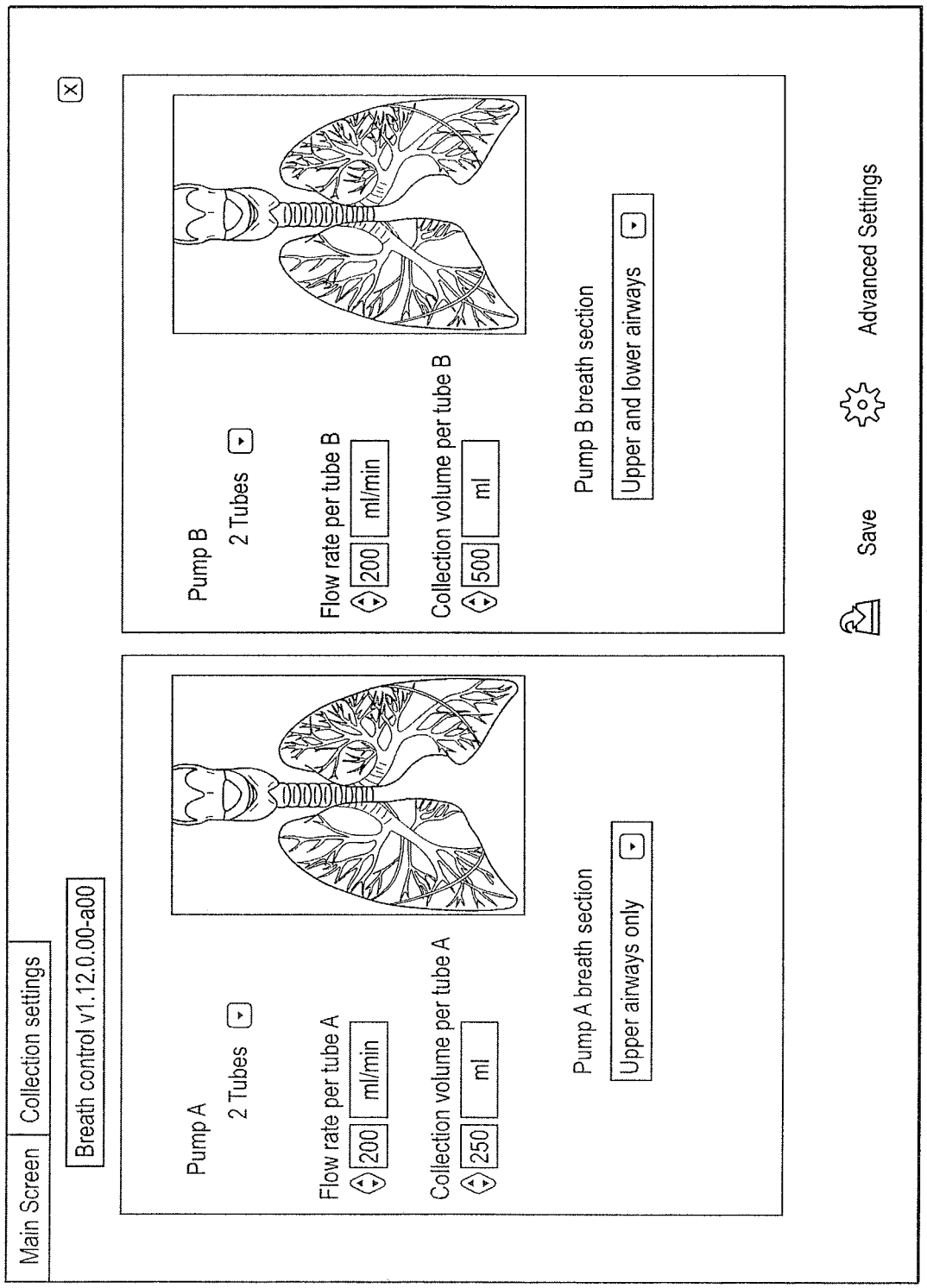
Figure 12C:
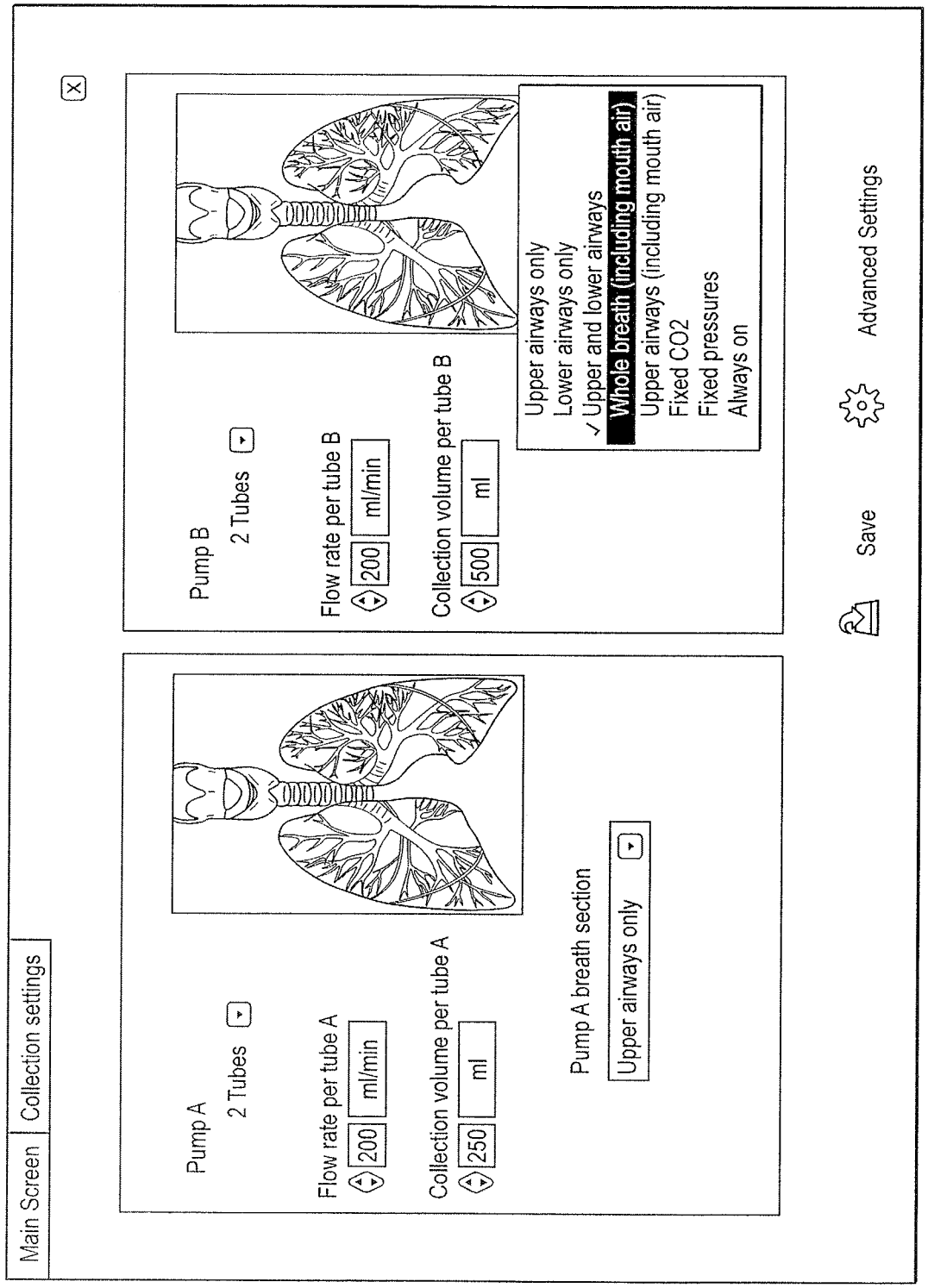
Figure 12D:
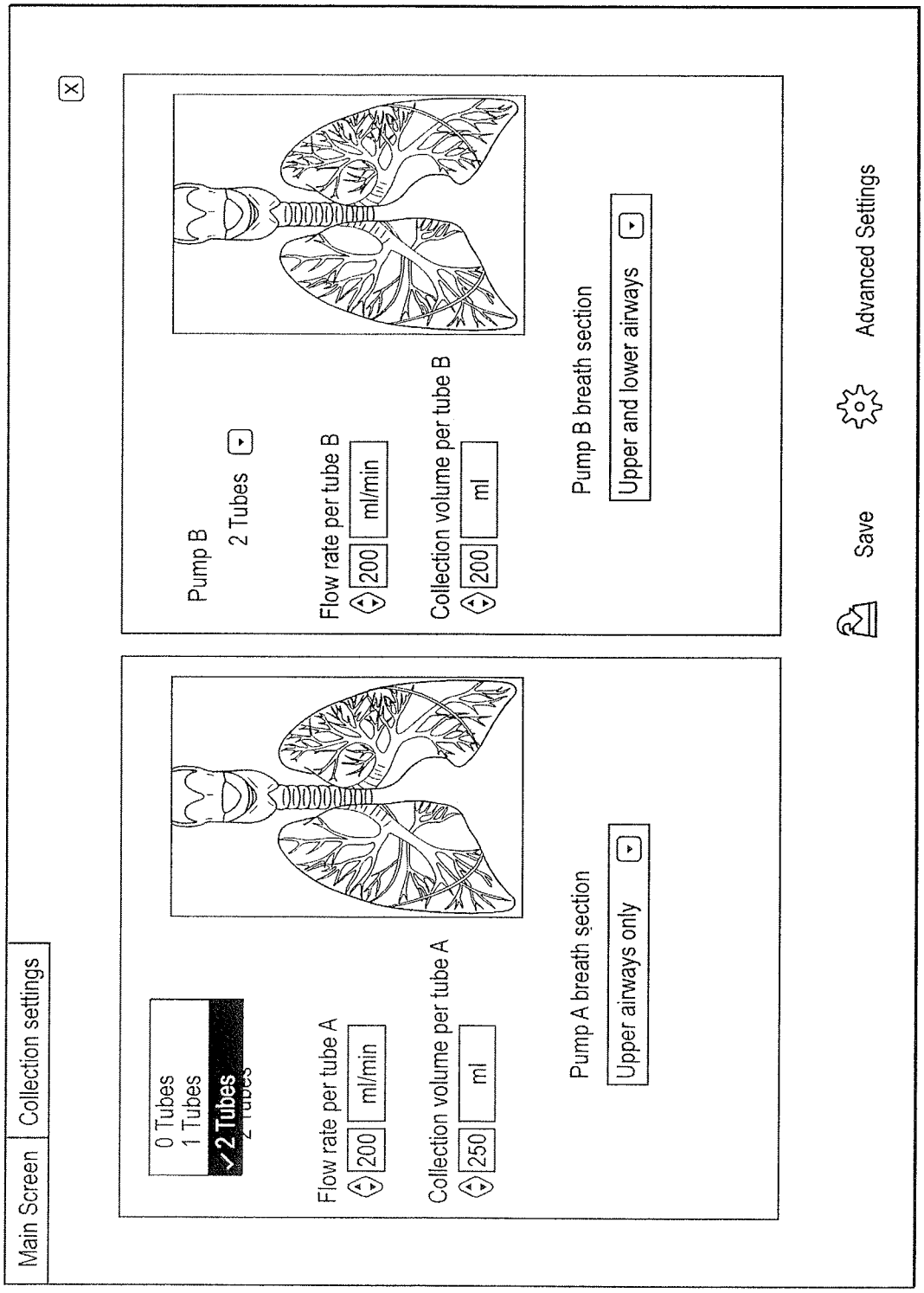
Figure 12F:
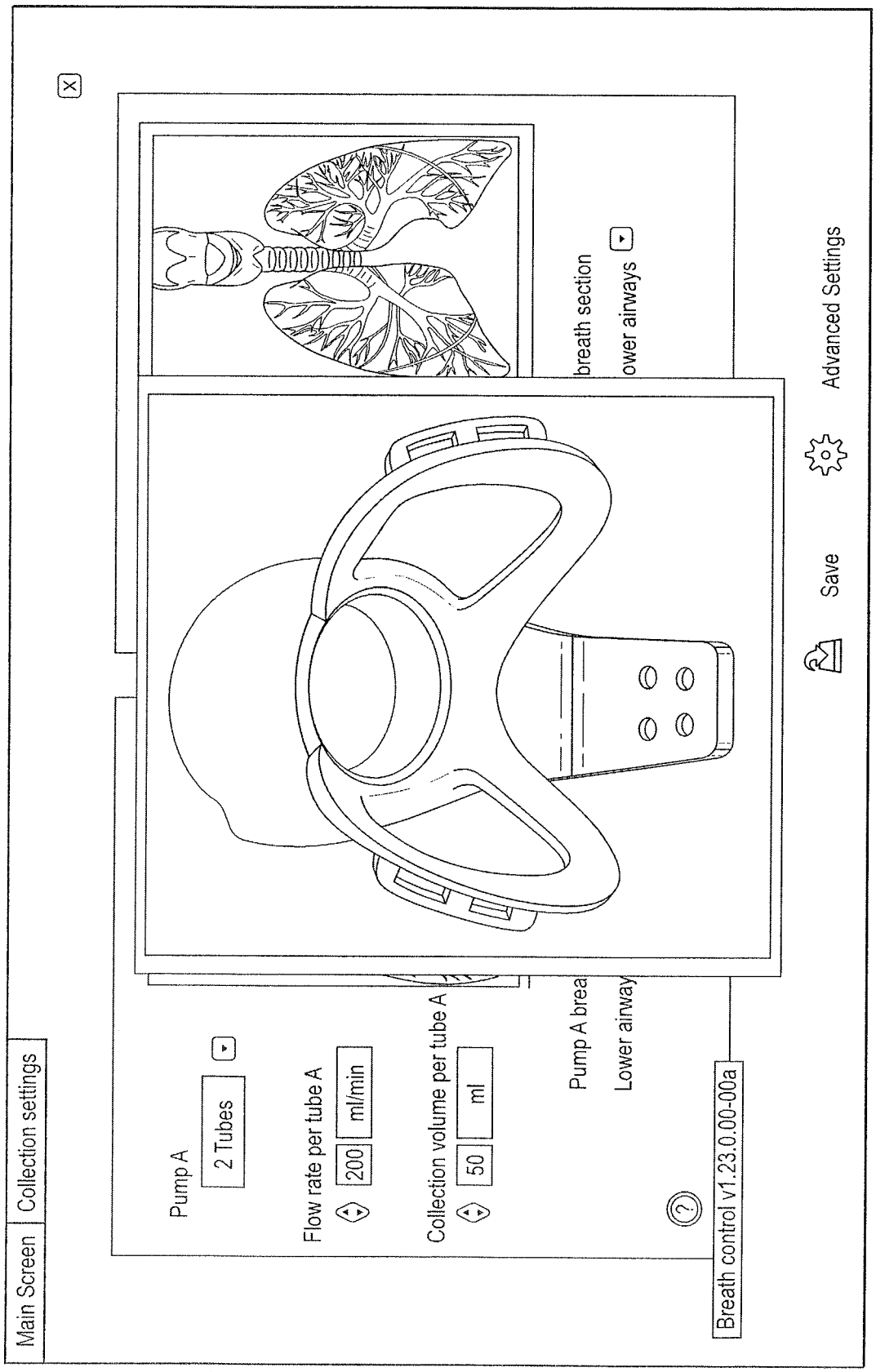

With description of one or more illustrated embodiments of device 10 being described above with reference to FIGS. 1-10, description now will be provided regarding the control board 32 and associated computing components and systems used in conjunction with operation of device 10. With reference now to FIG. 11, shown is a computer system 200, the components of which may be included in device 10 (e.g., control board 32).

The components of system 200 may include, but are not limited to, one or more processors or processing units 216, a system memory 228, and a bus 218 that couples various system components including system memory 228 to processor 216.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computing device 200 typically includes a variety of computer system readable media. Such media may be any available media that is accessible by device 200, and it includes both volatile and non-volatile media, removable and non-removable media.

System memory 228 can include computer system readable media in the form of volatile memory, such as random access memory (RAM) 230 and/or cache memory 232. Computing device 200 may further include other removable/non-removable, volatile/non-volatile computer system storage media. By way of example only, storage system 234 can be provided for reading from and writing to a non-removable, non-volatile magnetic media and/or Solid State Drives (SSD) (not shown and typically called a "hard drive"). Although not shown, a magnetic disk drive for reading from and writing to a removable, non-volatile magnetic disk, and an optical disk drive for reading from or writing to a removable, non-volatile optical disk such as a CD-ROM, DVD-ROM or other optical media may be associated with system 200. In such instances, each can be connected to bus 218 by one or more data media interfaces. Memory 228 may include at least one program product having a set (e.g., at least one) of program modules that are configured to carry out the functions of embodiments of device 10 described herein.

Program/utility 240, having a set (at least one) of program modules 215, such as underwriting module, may be stored in memory 228 by way of example, and not limitation, as well as an operating system, one or more application programs, other program modules, and program data. Each of the operating system, one or more application programs, other program modules, and program data or some combination thereof, may include an implementation of a networking environment. Program modules 215 generally carry out the functions and/or methodologies of embodiments of the invention as described herein.

Device 200 may also communicate with one or more external devices 214 such as a keyboard, a pointing device, a display 224, etc.; one or more devices that enable a user to interact with computing device 200; and/or any devices (e.g., network card, modem, etc.) that enable computing device 200 to communicate with one or more other computing devices. Such communication can occur via Input/Output (110) interfaces 222. Still yet, device 200 can communicate with one or more networks such as a local area network (LAN), a general wide area network (WAN), and/or a public network (e.g., the Internet) via network adapter 220. As depicted, network adapter 220 communicates with the other components of computing device 200 via bus 218. It should be understood that although not shown, other hardware and/or software components could be used in conjunction with device 200. Examples, include, but are not limited to: microcode, device drivers, redundant processing units, external disk drive arrays, RAID systems, tape drives, and data archival storage systems, etc.

Description of an Embodiment in Operation

The method of the invention is preferably performed using breath sampling apparatus as described above, which is made by Owlstone Medical Limited and known as "ReCIVA" apparatus.

The first step is that the subject fill in a form (the "ECRF" or Electronic Clinical Record Form). This includes details of age, smoking history, other disease history, what the subject last ate, and when etc. The answers to these questions are used to define some initial settings and parameters for the ReCIVA apparatus.

The mask is fitted to the subject, ideally so as to achieve an air-tight seal. The breath trace is suppressed if air leaks around the side of the mask. Since younger subjects (especially 6-11 year olds) breathe faster than adults, it can be difficult to discriminate between a young person, and an adult with a leaking mask fit. Accordingly, inputting age and weight into the starting data can help ReCIVA to overcome these difficulties.

On powering up, the device takes a few seconds to calibrate and determine an appropriate pump setting to achieve the desired flow rate of air into the mask and (in theory) detects any leaks in the system.

The device then has an initial "learning" period of about 30 seconds, to collect data on how the subject is breathing. In particular, the device looks to measure the amplitude of the breaths (i.e. the peak to trough difference in absolute pressure) and also the first differential of the pressure in order to map change points between inhalation and exhalation. This learning period enables the device to calculate the initial trigger points for collection of "upper breath" and "lower breath" fractions, but these are continuously updated during the sampling period to reflect any alterations in the subject's breathing pattern. In particular in practice the inventors have found that subjects are a little nervous when using the device for the first time and tend to breathe more quickly and more shallowly, but after a few minutes, they relax and breathe more naturally. The device is able to detect this and adjust the timing of the trigger points for collection appropriately. Sampling occurs by causing operation of small piezo electric suction disc pumps which draw the exhaled air into the sorbent tubes for collecting sample. The sampling period is around 2 seconds per breath. Sampling typically has to be continued intermittently for around 10 minutes in order to collect a sufficient volume of exhaled air fractions in the sorbent tubes. Assuming a respiration rate of 14 breaths per minute (average for an adult), this means there are around 140 exhalations required to collect sufficient sample.

At present the ReCIVA is preferably used in conjection with "CASPAR" (Clean Air Supply, in which air fed into the mask is passed through an activated carbon filter). This helps to remove extraneous compounds from the atmosphere which would otherwise complicate the analysis of the exhaled breath.

Figure 13:
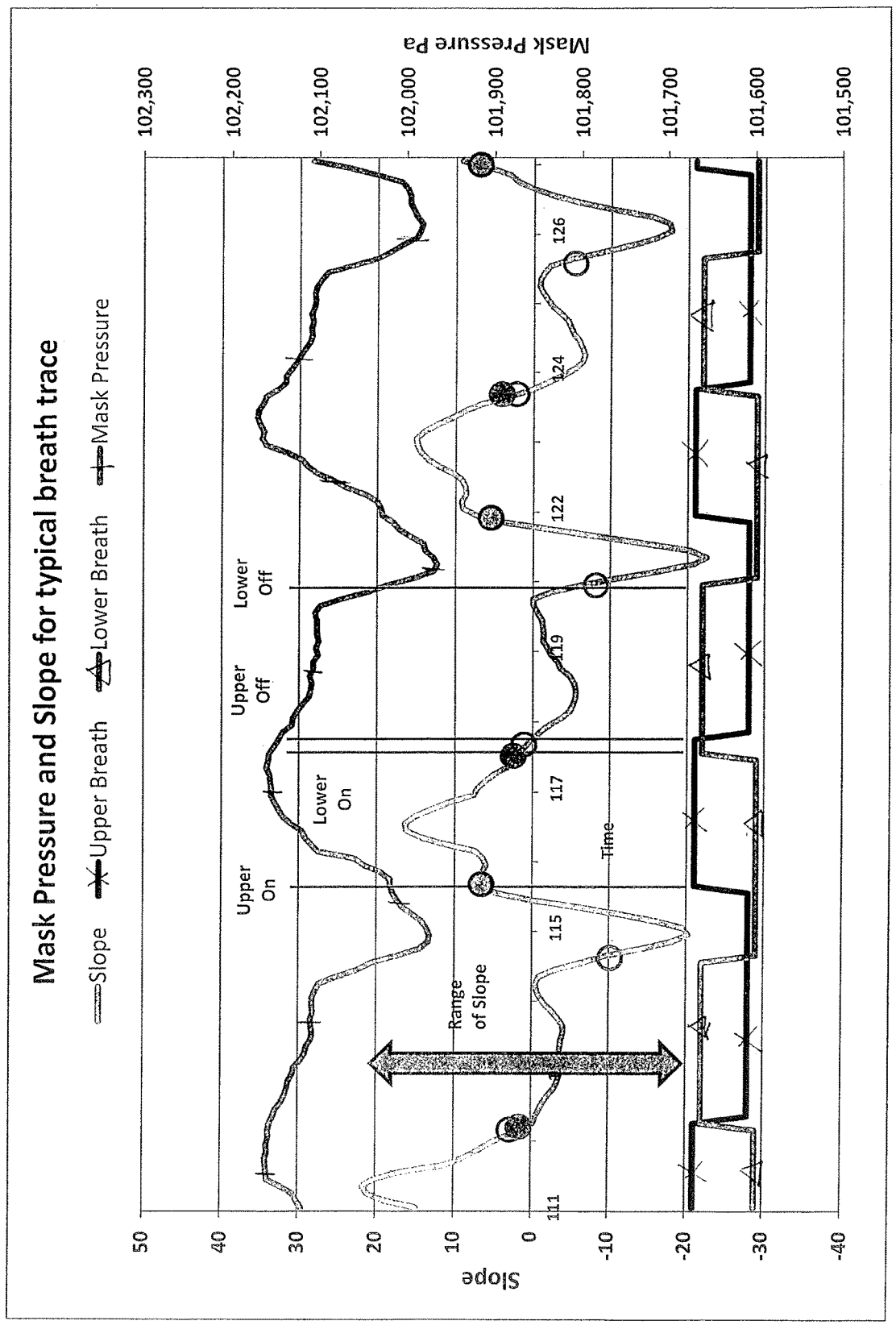
FIG. 13 is a graph showing typical data obtained for performing a method in accordance with the invention.

FIG. 13 illustrates typical readings obtained when performing one embodiment of the method of the invention. The method involves substantially continuous monitoring of the pressure inside the mask partion of the apparatus ("Mask Pressure"), which is the upper trace in the graph. The Figure shows the value over three nearly complete breath cycles by a subject. As would be expected, the mask pressure falls as the subject inhales, and increases when the subject exhales. The magnitude of the mask pressure is shown on the scale on the right-hand side of the Figure, in Pascals. The time, in seconds (from 111 to 126) is indicated by the numerals across the centre of the graph. As can be seen each complete breath cycle takes about 4-5 seconds.

From the raw data for mask pressure, the apparatus calculates the rate of change of mask pressure, and this calculated value ("Slope") is shown by the lower trace on the graph, with a value from about +20 to −20 (indicated by the scale on the left-hand side of the Figure). The "Slope" is actually a filtered derivative. The filtering can be best approximated by a flat average of six readings, delayed by one sample period:

$$\text{Slope}_N = \text{average } (P_{n-1} \text{ to } P_{n-6}) - \text{average } (P_{n-2} \text{ to } P_{n-7})$$

The system then maintains a running average of the maximum and minimum of slope, and hence its range, over a time period of about 30 seconds (i.e. six breath cycles). The range of Slope is indicated on the graph in FIG. 13 by the large vertical double-headed arrow.

The value of the Slope as a proportion of the Range of Slope, is used to calculate various trigger points, when the sample pumps are turned on or off so as to selectively sample desired portions of the subject's exhaled breath. The apparatus comprises an "upper airway pump" which is actuated to collect a sample of air from the subject's upper airway, and a "lower airway pump" which is actuated to collect a sample of air from the subject's lower airway. The two plots at the bottom of FIG. 13 indicate the status of the upper airway pump (□×□) and lower airway pump (□Δ□): the pump is active when the plot is high, and inactive when the plot is low.

The upper airway pump is turned on when Slope gets above the scaled Start Upper Airway threshold. If this is set to the default of 5 it is turned on when Slope is 50% of its range above zero.

The upper airway pump is turned off when Slope gets below the End Upper Airway threshold. If this is set to the default of 1 it is turned off when Slop is 10% of its range above zero.

The lower airway pump is turned on when the pressure is at least 20% down from its maximum and Slope is decreasing.

The lower airway pump is switched off at 40% above the minimum pressure. There is no alteration available on this point.

The End Upper Airway threshold must be set lower than the Start Upper Airway threshold. If it is set higher the threshold will be reached immediately after the pump is turned on resulting in it being almost instantly switched off again and no upper breath being collected.

It is to be understood that the above-described arrangements are only illustrative of the application of the principles of the illustrated embodiments. Numerous modifications and alternative arrangements may be devised by those skilled in the art without departing from the scope of the illustrated embodiments, and the appended claims are intended to cover such modifications and arrangements.

What is claimed is:

1. A method for selectively capturing one or more portions of a patient's breath using a portable microprocessor-controlled breath collection apparatus comprising a face mask, and a plurality of sorbent tubes protrude through holes formed in the face mask, the method comprising:
    detect one or more parameters regarding the patient's breath during a breathing routine;
    determine one or more data points from the detected one or more parameters wherein the one or more data points identifies one or more portions of the patient's breath to capture;
    capture one or more portions of the patient's breath during the breathing routine; and monitor the pressure of the patient's breath inside the face mask in order to detect a poorly-fitting mask and provide feedback to a user if detected.

2. The method as recited in claim 1, wherein the one or more portions of the patient's breath is captured to one or more of the sorbent tubes.

3. The method as recited in claim 1, wherein the patient's breath includes the air inhaled or exhaled from the pulmonary system, nasopharynx or oropharynx.

4. The method as recited in claim 1, wherein the one or more parameters or data points are detected simultaneous to breath capture.

5. The method as recited in claim 1, wherein the one or more detected parameters or the one or more determined data points are updated continuously during the breathing routine.

6. The method as recited in claim 1, further including capturing the same or different portions of breath to different sorbent tubes during the same breathing routine.

7. The method as recited in claim 1, wherein the one or more data points identifies an alveolar, bronchiolar, nasopharyngeal, oropharyngeal, gastro-intestinal, or other portion of the patient's breath or any combination of these portions.

8. The method as recited in claim 1, wherein the one or more parameters detected is indicative of the $CO_2$ content of the patient's breath.

9. The method as recited in claim 8, wherein the $CO_2$ content is indicative of a portion of breath which is captured.

10. The method as recited in claim 9, wherein the portion of breath which is captured is one of alveolar, bronchiolar, nasopharyngeal, oropharyngeal, gastro-intestinal, or other portion of the patient's breath or any combination of these portions.

11. The method as recited in claim 1, wherein the one or more parameters detected is indicative of the pressure level of the patient's breath.

12. The method as recited in claim 11, wherein the pressure level is indicative of a portion of breath which is captured.

13. The method as recited in claim 12, wherein the portion of breath which is captured is one of alveolar, bronchiolar, nasopharyngeal, oropharyngeal, gastro-intestinal, or other portion of the patient's breath or any combination of these portions.

14. The method as recited in claim 1, wherein the one or more data points determined is indicative of both the $CO_2$ content and pressure level of the patient's breath.

15. The method as recited in claim 14, wherein the $CO_2$ content and pressure level are indicative of a portion of breath which is captured.

16. The method as recited in claim 15, wherein the portion of breath which is captured is one of alveolar, bronchiolar, nasopharyngeal, oropharyngeal, gastro-intestinal, or other portion of the patient's breath or any combination of these portions.

17. The method as recited in claim 1, wherein the one or more data points determined are a mathematical function of the one or more parameters detected.

18. The method as recited in claim 1, wherein the one or more parameters detected are filtered to remove the effects of breathing irregularities due to coughing, talking, or rapid or slow breaths.

19. The method as recited in claim 1, further including providing feedback to the user, through a connected computer interface, to:
improve the efficiency or accuracy of breath collection;
to warn of faults or to warn of inappropriate ventilation causing either hypoventilation or hyperventilation, as indicated by hypercapnia, hypocapnia, bradypnea, or tachypnea.

20. The method as recited in claim 1, further including determining a volume of the patient's breath to be captured.

21. The method as recited in claim 1, further including stopping the capture of the patient's breath at one or more designated time points or collection volumes.

22. The method as recited in claim 1, wherein the sorbent tubes are mounted unevenly in a block, so that the block of sorbent tubes will fit inside the face mask only in an intended orientation.

23. A method for selectively capturing one or more portions of a subject's breath using a portable microprocessor-controlled breath collection apparatus comprising a face mask, and a plurality of sorbent tubes protrude through holes formed in the face mask, the method comprising the steps of:
measuring, in absolute or relative terms, at least once, during each sampled breath cycle of a subject at least one parameter relating to the subject's breathing;
using the aforementioned measurement or measurements to identify and selectively sample one or more desired portions of the subject's breath; and
monitoring the pressure of the subject's breath inside the face mask in order to detect a poorly-fitting face mask and providing feedback to a user if detected.

24. The method according to claim 23, wherein said at least one parameter comprises one or more of the following: an absolute pressure measurement; a relative pressure measurement; an $O_2$ partial pressure measurement; and a $CO_2$ partial pressure measurement.

25. The method according to claim 23, wherein said at least one parameter comprises a relative measurement.

26. The method according to claim 23, comprising the measurement of at least two parameters relating to the subject's breathing.

27. The method according to claim 23, wherein said at least one parameter is measured a plurality of times during each sampled breath cycle of the subject.

28. The method according to claim 27, wherein said at least one parameter is substantially continuously monitored, at least during exhalation.

29. The method according to claim 28, wherein said at least one parameter is also substantially continuously monitored during inhalation.

30. The method according to claim 23, wherein the said at least one parameter is the amplitude or difference in pressure between peak and trough in absolute pressure during a sampled breath cycle.

31. The method according to claim 30, further comprising the step of calculating the $1^{st}$ differential of the measured amplitude or difference in pressure.

32. The method according to claim 23, wherein the measurement of said at least one parameter is compared with a respective threshold to determine when during the breath cycle to selectively capture a portion of the subject's breath.

33. The method according to claim 23, further comprising the step of inputting, into a digital electronic memory or digital electronic control device, data relating to one or more of: the age of the subject, the weight of the subject, the medical history of the subject, the smoking history of the subject, and any current known or suspected medical conditions of the subject.

34. The method according to claim 23, wherein the sorbent tubes are mounted unevenly in a block, so that the block of sorbent tubes will fit inside the face mask only in an intended orientation.

* * * * *